United States Patent [19]

Lifson et al.

[11] Patent Number: 4,869,903

[45] Date of Patent: * Sep. 26, 1989

[54] METHOD OF SELECTIVELY INHIBITING HIV

[75] Inventors: Jeffrey D. Lifson, Menlo Park; Michael S. McGrath, Burlingame, both of Calif.; Hin-Wing Yeung, Kowloon, Hong Kong; Kuo Hwang, Danville, Calif.

[73] Assignee: Genelabs Incorporated, Redwood City, Calif.

[*] Notice: The portion of the term of this patent subsequent to Jan. 3, 2006 has been disclaimed.

[21] Appl. No.: 179,274

[22] Filed: Apr. 8, 1988

Related U.S. Application Data

[63] Continuation-in-part of Ser. No. 56,558, May 29, 1987, Pat. No. 4,795,739.

[51] Int. Cl.[4] .................... A61K 37/02; A61K 35/78; A61K 35/80; C07G 7/00
[52] U.S. Cl. .................................. 424/195.1; 514/8; 514/885
[58] Field of Search .................. 514/8, 12, 21, 885; 424/88, 91, 195.1; 530/370, 379, 806

[56] References Cited

U.S. PATENT DOCUMENTS 3,104,204 9/1963 Olson .................................. 424/117
3,104,208 9/1963 Olson et al. ........................ 435/70
3,230,153 1/1966 Olson et al. ........................ 435/171
3,842,062 10/1974 Eastman ............................. 530/411

OTHER PUBLICATIONS

Armstrong, W. H., Presented at the International Conference on Aids, Jun. 23-25, 1986, Paris.
Barbieri, L. et al, Biochem J. 182:633 (1979).
Barbieri, L. et al, Biochem J. 186:443 (1980).
Barbieri, L. et al, Biochem J. 203:55 (1982).
Barnes, D. M., Science, 235:964 (1987).
Broder et al, Lancet ii:627 (1985).
Broder et al, Nature 325-:773 (1987).
Chan, W. Y. et al, Contraception, 29:91 (1984).
Chayt, K. J. et al, JAMA, 256:2356 (1986).
Coffin, J. et al, Science, 232:697 (1986).
Crowe, S., Mills, J., and McGrath, M. S., submitted for publication.
Curran, J. W. et al, Science, 229:1352 (1985).
Dalgliesh, A. G. et al, Nature, 312:763 (1984).
Fahey, J. L., Am J Me7, 76:95 (1984).
Falasca, A. et al, Biochem J, 207:505 (1982).
Foa-Tomasi, L. et al., Arch Virol, 71:323 (1982).
Foung, S. K, H. et al., Human Hybridomas and Monoclonal.
Antibodies, E. G. Engleman et al., eds, Plenum Press, N.Y., p. 437 (1985).
Gartner S., Science, 233:215 (1986a).
Gartner S. et al., JAMA, 256, 2365 (1986b).
Gaspani-Compani, A., Biochem J., 186:439 (1980).
Gu, Zi-wei et al., Acta Chemica Sinica, 43:943 (1984).
Ho, D. D. et al., J Clin Invest, 77:1712 (1986).
Hsu, K. J. et al., Acta Zool Sin, 22:149 (1976).
Hoffman, A. E. et al., Virology, 147:326 (1985).
Hwang, Y. N., Chinese J Integrated Trad and Western Medicine, 7:154 (1987).
Irvin, J. D., Pharmacol Ther, 21:371 (1983).
Jilka, C. et al., Cancer Res., 43:5151 (1983).
Kao, H. et al., Acta Biol Exp Sin, 11:253 (1978).
Kennedy, R. C. et al., Science, 231:1556 (1986).

(List continued on next page.)

Primary Examiner—John Kight
Assistant Examiner—Nathan M. Nutter
Attorney, Agent, or Firm—Peter J. Dehlinger

[57] ABSTRACT

A method of inhibiting HIV replication in and cellular proliferation of HIV-infected cells. The infected cells are exposed to a single-chain ribosome inactivating protein, at a protein concentration and for an exposure period sufficient to produce a substantial reduction in (a) the level of HIV antigen or reverse transcriptase associated with the infected cells, (b) the ratio of viability of infected/uninfected T cells, and/or (c) the ratio of HIV antigen/cellular antigen in infected macrophages. The method is used to treat HIV infection in humans.

20 Claims, 14 Drawing Sheets

OTHER PUBLICATIONS

Kezhan, Pan et al., Supplement of Proc of China–Japan Bilateral Symposium on Biophys, Wuxi, China (May 1985).
Klatzmann, D. et al., Science, 225:59 (1984a).
Klatzmann, D. et al., Nature, 312:767 (1984b).
Koenig, S. et al., Science, 233:1089 (1986).
Kubota, S. et al., Biochim Biophys Acta, 871:101 (1986).
Kuo-Fen, C. et al., Obs and Gyn, 59(4):494 (1982).
Law, L. K. et al., J Reprod Fert, 69:597 (1983).
Licastro, F. et al., Virchows Arch B Cell Path, 33:257 (1980).
Lifson, J. D. et al., Science, 232:1123 (1986a).
Lifson, J. D. et al., Nature, 323:725 (1986b).
Lifson, J. D. et al., J. Exp Med, 164:2101 (1986c).
Lifson, J. D., J Exp Med, 164:2101 (1986c).
Lin, J. Y. et al., Cancer Res, 30:2431 (1970).
Lin, J. Y. et al., Toxicon, 16:653 (1978).
Maddon, J. P., Cell, 47:333 (1986).
McCormick, J. B. et al., Lancet, ii:1367 (1984).
McDougal, J. S., Science, 231:382 (1985a).
McDougal, J. S. et al., J Immunol, 135:3151 (1985b).
McDougal, J. S. et al., J Immunol, 137:2937 (1986).
Olnes, S. et al., in Molecular Action of Toxins and Viruses, 51–105 Elsevier, Amsterdam (1982).
Popovic, M. et al., Science, 224:497 (1984).
Roberts, W. K., Biochemistry, 18:2615 (1979).
Salvedt, E., Biochim, Biophys Acta, 451:536 (1976).
Sodroski, J. et al., Nature, 322:470 (1986).
Spreafico, F. et al., Int. J. Immunopharmac, 5(4):335 (1983).
Stanley, W. S. et al., Proc Nat Acad Sci, U.S.A., 76:303 (1979).
Steicher, H. Z. et al., JAMA, 256:2390 (1986).
Stirpe, F. et al., J Biol Chem, 255:6947 (1980).
Stirpe, F. et al., Biochem J. 195:399 (1981).
Takemoto, D. J. et al., Prep Biochem, 12(4):355 (1982).
Takemoto, D. J. et al., Prep Biochem, 13(4):371 (1983a).
Takemoto, D. J. et al., Prep Biochem, 13(5):397 (1983b).
Wang, Yu et al., Int Symposium on Org Chem of Medicinal Natural Products, Shanghai, China (Nov., 1985).
Xiong, Y. Z. et al., Acta Zool Sin, 11:236 (1976).
Xuejan, Z. et al., Nature, 321:477 (1986).
Yarochan, R. et al., Lancet, i:575 (1986).
Yarochan, R. et al., Lancet, i:132 (1987).
Yeung, H. W. et al., in Adv in Chinese Medicinal Materials Res, edited by H. M. Change et al., World Scientific Pub, Singapore p. 311 (1985).
Res, edited by H. M. Change et al., World Scientific Pub, Singapore p. 311 (1985).
Yeung, H. W. et al., Int J. Peptide Protein Res, 27:325 (1986).
Fernandez-Puentes et al., Cell, vol. 20, 769–775, Jul. (1980), Viral Infection Permeabilizes Mammalian Cells to Protein Toxins.
Fernandez-Puentes, Mollecular and Cellular Biochemistry 50, 185–191 (1983), Permeability to alpha sarcin in virus-infected cells.
Calderwood, S. B. et al., Proc Natl Acad Sci U.S.A., 84:4364–4368 (Jul. 1987).
Conde, F. P., FEMS Microbiology Letters 4:349–55 (1978) et al.
Coleman, W. H., Biochemuta et Biophysica Aca, 696:239–244 (1982) et al.
Endo, Y., J of Biol Chem. vol. 267 No. 15 9054–9060 (1982) et al.
Endo, Y., J of Biol Chem, vol. 262 No. 12 5908–5912 (1987) et al.
Fernandez-Luna, J. L. Biochemistry 24:861–867 (1985) et al.
Fernandez-Puentes, C., Cell 20:769–775 (Jul. 1989) et al.
Fernandez-Puentes, C., Mol Cell Biochem 50:185 (1983).
Foa-Tomasi, L., Archives of Virology 71:323–332 (1982) et al.
Gasperi-Campani, A., FEBS Letters 76:2:173–176 (1977) et al.
Grasso, S., Phytophathology 68:199–205 (1978) et al.
Irvin, J. D. et al., Archives of Biochemistry and Biophysics, vol. 200 No. 2, 418–425 (4/1/80).
Irvin, J. D., Archives of Biochemistry and Biophysics 169:522–528 (1975).
Lopez-Otin, C. et al., Eur J Biochem 143:621–634 (1984).
Maraganore, J. M., J of Biological Chem, 262:24:11628–11633 (1987) et al.
Olsnes, S., Molecular Action of Toxins and Viruses, et al.
Elsevier Biomedical Press (1982).

(List continued on next page.)

OTHER PUBLICATIONS

Olsnes, S., Nature, 328:474-475 (Aug. 1987).
Olson, B. H., Applied Microbiology, 13:3:322-326 (May 1965), et al.
Olson, B. H. et al., Applied Microbiology 13:3:314-321 (May 1985).
Ragetli, H. W. J. et al., Virology 18:232:240 (1962).
Rodriquez, R. et al., Biochemical and Biophysical Research Communications, 108:1:315-321 (9/16/82).
Sacco, G. et al., J of Biol Chem, 258:9:5811-5818 (1983).
Sarngadharan, M. G. et al., Fundamental Virology, Chapt. 32, pp. 681-707.
Sargiacomo, M. et al., FEBS 0154 157:1:150-154 (1983).
Schindler, D. G., Nucleic Acids Research, vol. 4 No. 4 (Apr. 1977).
Stevens, W. A. et al., Experientia 37 (1981).
Takemoto, D. J. et al., Biochemical and Biophysical Research Communications, vol. 94 No. 1 (5/14/80).
Xuejun Z. et al., Nature, 321:477-478 (May 1986).
Yeung, H. W. et al., Advances in Chinese Medicinal Materials Research, 311-318 (1985).
Kronke, M. et al., Blood, 65:6:1416-1421 (1985).
Kronke, M. et al., Cancer Research, 46:3295-3298 (Jul. 1986).

METHOD OF SELECTIVELY INHIBITING HIV

The present invention is a continuation-in-part of copending U.S. patent application for "Method of Inhibiting HIV", Ser. No. 056,558, filed May 29, 1987.

FIELD OF THE INVENTION

The present invention relates to a method of inhibiting the expression of HIV proteins in human T cells and monocyte/macrophages, as a method of treating HIV infection in humans.

REFERENCES

Armstrong, W. H., Presented at the International Conference on AIDS, 23–25 June, 1986, Paris.
Barbieri, L. et al, Biochem J, 182:633 (1979)
Barbieri, L. et al, Biochem J, 186:443 (1980).
Barbieri, L. et al, Biochem J, 203:55 (1982)
Barnes, D. M., Science, 235:964 (1987)
Broder et al, Lancet, ii:627 (1985).
Broder et al, Nature 325:773 (1987)
Calderwood, S. B., et al, Proc Nat Acad Sci, U.S.A., 84:4364 (1987)
Chayt, K. J. et al, JAMA, 256:2356 (1986).
Coffin, J. et al, Science, 232:697 (1986)
Coleman, W. H., et al, Biochem Biophys Acta, 696:239 (1982)
Conde, F. P., et al, FEMS, Microbiology Letters, 4:349 (1978)
Crowe, S., Mills, J., and McGrath, M. S., AIDS Res. and Human Retrovirus 13:135 (1987).
Dalgliesh, A. G. et al, Nature, 312:763 (1984).
Endo, Y., et al, J Biol Chem, 257:9054 (1982).
Endo, Y., et al, J Biol Chem, 262:5908 (1987).
Fahey, J. L., Am J Med, 76:95 (1984).
Falasca, A. et al, Biochem J, 207:505 (1982).
Fernandez-Puentes, C., Mol Cell Biochem, 50:185 (1983)
Fernandez-Puentes, C., et al, Cell, 20:769 (1980).
Foa-Tomasi, L. et al, Arch Virol, 71:323 (1982). York, p.437 (1985).
Foung, S. K. H. et al, Human Hybridomas and Monoclonal Antibodies, E. G. Engleman et al, eds, Plenum Press, New York, p. 437 (1985).
Gartner S., Science, 233:215 (1986a).
Gartner S. et al, JAMA, 256, 2365 (1986b).
Gaspani-Campani, A., Biochem J, 186:439 (1980).
Gu, Zi-wei, et al, Acta Chemica Sinica, 43:943 (1984).
Grasso, S., et al, Phytopathology, 68:199 (1978).
Ho, D. D. et al, J Clin Invest, 77:1712 (1986).
Hoffman, A.D. et al, Virology, 147:326 (1985).
Hwang, Y. N., Chinese J Integrated Trad and Western Medicine, 7:154 (1987).
Irvin, J. D., Archives Biochem Biophys, 169: 522 (1975).
Irvin, J. D., et al, Archives Biochem Biophys, 200(2):418 (1980).
Irvin, J. D., Pharmacol Ther, 21:371 (1983).
Jimenez, A., et al, Ant Agent Chemother, 3:729 (1973).
Kennedy, R. C., et al, Science, 231:1556 (1986).
Kezhan, Pan, et al, Supplement of Proc of China-Japan Bilateral Symposium on Biophys, Wuxi, China (May, 1985).
Klatzmann, D., et al, Science, 225:59 (1984a).
Klatzmann, D., et al, Nature, 312:767 (1984b).
Koenig, S., et al, Science, 233:1089 (1986).
Kuo-Fen, C. et al, Obs and Gyn, 59(4):494 (1982).
Law, L. K. et al, J Reprod Fert, 69: 597 (1983).
Lifson, J. D. et al, Science, 232:1123 (1986a).
Lifson, J. D. et al, Nature, 323:725 (1986b).
Lifson, J. D., J Exp Med, 164:2101 (1986c).
Lin, J. Y., et al, Cancer Res, 30:2431 (1970).
Lin, J. Y., et al, Toxicon, 16:653 (1978).
Maddon, J. P., Cell, 47:333 (1986).
Maraganore, J. M., et al, J Biol Chem, 262:11628 (1987).
McDougal, J. S., Science, 231:382 (1985a).
McDougal, J. S., et al, J Immunol, 135:3151 (1985b).
McDougal, J. S., et al, J Immunol, 137:2937 (1986).
Olsnes, S. et al in Molecular Action of Toxins and Viruses, 51–105 Elsevier, Amsterdam (1982).
Olsnes, S., Nature 328:474 (1987).
Olson, B. H. et al, U.S. Patent No. 3,104,208 (1963).
Olson, B. H. et al, U.S. Patent No. 3,230,153 (1966).
Olson, B. H., et al, App Microbio, 13(3):314 (1965a).
Olson, B. H., et al, App Microbio, 13(3):322 (1965b).
Popovic, M. et al, Science, 224:497 (1984).
Roberts, W. K., Biochemistry, 18:2615 (1979).
Rodriguez, R., et al, Biochem Biophys Res Commun, 108(1):315 (1982).
Sacro, G., et al, J Biol Chem, 258:5811 (1983).
Salvedt, E., Biochim, Biophys Acta, 451:536 (1976).
Sarngadharan, M. G., et al, in *Fundamental Virology* (Fields, B. N., et al eds) Raven Press, New York (1986) pp. 681–707.
Schindler, D. G., et al, Nuc Acid Res, 4:1097 (1977).
Sodroski, J., et al, Nature, 322:470 (1986).
Spreafico, F. et al, Int. J. Immunopharmac, 5(4):335 (1983).
Steicher, H. Z. et al, JAMA, 256:2390 (1986).
Stirpe, F., et al, J Biol Chem, 255:6947 (1980).
Stirpe, F., et al, Biochem J, 195:399 (1981).
Wang, Yu, et al, Int Symposium on Org Chem of Medicinal Natural Products, Shanghai, China (November, 1985).
Xuejan, Z. et al, Nature, 321:477 (1986).
Yarochan, R. et al, Lancet, i:575 (1986).
Yarochan, R. et al, Lancet, i:132 (1987).

BACKGROUND

Human Immunodeficiency Virus (HIV) is a retrovirus which is the etiological agent for acquired immune deficiency syndrome (AIDS) and a spectrum of related disorders (Coffin). The virus is transmitted by parenteral inoculation and/or intimate sexual contact. It is estimated that approximately 2 million people in the United States are infected with HIV at present, and current projections are that a majority of those now infected will develop AIDS or a significant clinical HIV-related disease within a 7–10 year follow-up period (Barnes).

HIV is tropic and cytopathic for cells which express the cell surface differentiation antigen CD4 (T4, leu3). The viral tropism is believed to result from interactions between CD4 and the envelope glycoprotein of HIV. These interactions appear to be involved in the process by which HIV infects susceptible cells, and also underlie the mechanism by which HIV induces cell fusion in T cells (Lifson, 1986a, 1986b; Dalgleish; Klatzman, 1984a, 1984b; Maddon; McDougal, 1985a, 1985b; Sodroski). The cell fusion process, which can lead to cell death, may, in turn, contribute to the progressive depletion of CD4 cells which characterizes AIDS, and which may be a factor contributing to HIV-induced immunocompromise and its secondary consequences, opportunistic infections and neoplasms (Fahey).

The host cell range for the Human Immunodeficiency Virus (HIV) includes, in addition to CD4+ T cells, cells of the mononuclear phagocytic lineage, including peripheral blood monocytes, tissue macrophages, (Steicher), Langerhans cells of the skin, and dendritic reticulum cells (Armstrong) within the lymph nodes. Mononuclear phagocytes may be a primary target cell for HIV infection within the central nervous system (Koenig; Gartner, 1986b). Cells of the macrophage lineage are likely to represent a major viral reservoir in vivo, and either alone or through their interactions with T cells, may contribute to the development and pathogenesis of AIDS and related clinical diseases (Crowe). Experiments conducted in support of the present invention suggest that a large percentage of monocyte/macrophages derived from HIV-infected individuals are capable of expressing HIV antigens, indicating widespread infection of the macrophage precursors. There is also evidence that macrophages expressing the HIV surface antigen may interact and fuse with CD4+ T cells, leading to destruction of the crucial T cells (Crowe).

Intensive efforts to develop therapies which can prevent or block the development of serious clinical symptoms in HIV-infected indviduals are under way. For the most part, these efforts have focused on the use of nucleoside analogue drugs which inhibit the viral reverse transcriptase enzyme (Yarochan, 1986, 1987; Broder, 1985, 1987). These drugs would be expected to selectively inhibit new viral infection of cells, such as T cells and monocyte/macrophages, since reverse transcriptase is required for early viral infection. However, once viral infection is established in a cell, and viral replication is then carried out using host cell enzymes, the reverse transcriptase inhibitors would be expected to have limited inhibitory effect on viral replication and expression of viral antigens on the host cell surface. In vitro studies have demonstrated HIV replication even in the continued presence of nucleoside analogues in prolonged culture. Although indications of some beneficial clinical effects have been observed, the early clinical testing results have provided little evidence that these drugs will be effective against later-stage progression of HIV infection to serious clinical diseases.

SUMMARY OF THE INVENTION

It is one general object of the invention to provide a method of selectively inhibiting HIV replication and proliferation of HIV infected human T cells and mononuclear phagocytic lineage cells.

A related object of the invention is to provide a method of inhibiting HIV antigen expression in HIVinfected cells.

Another related object is to provide a method of selectively inhibiting HIV antigen expression in mononuclear phagocytic lineage cells.

It is yet another object of the invention to provide a method of treating HIV infection in humans.

The discovery that viral expression and cell proliferation in HIV-infected T cells and monocyte/macrophages can be selectively inhibited by two plant proteins—trichosanthin (TCS), and momorcharin (MMC)—was described in the above, earlier filed patent application for "Method of Inhibiting HIV". An important aspect of the discovery was the finding that viral inhibition in HIV-infected cells could be achieved at concentrations of TCS or MMC which were substantially non-toxic to uninfected cells. This selective effect was evidenced by a marked decrease in viral antigen associated with HIV-infected cells, and in measurable reverse transcriptase activity, several days after exposure to TCS or MMC, without a significant decrease in expression of non-viral protein in non-infected cells. Another aspect of the selective inhibitory effect of TCS and MMC which was observed was a substantial loss of cell viability in HIV-infected cells, at an MMC or TCS concentration which did not significantly reduce the viability of non-infected cells. Typically, these selective inhibition effects were seen at TCS or MMC concentrations between about 0.01–3.0 ug/ml.

As discussed in the earlier filed application, the selective inhibitory effect of TCS and MMC may be related to the proposed ribosome inhibitory activity of these proteins. MMC is a potent inhibitor of protein synthesis in a cell-free system (Barbieri, 1982); and it has been speculated, from the observed amino acid homology between TCS and the A chain of ricin, that TCS may have ribosome inactivating properties similar to ricin and various single-chain plant proteins or glycoproteins which have N-glycosidase activity, and which have been reported to inactivate ribosomes by glycoside cleavage at one or more selected sites in ribosomal RNA (rRNA).

It has now been discovered that a broad range of single-chain proteins with ribosome inactivating activity, including gelonin, various species of pokeweed anti-viral proteins, alpha-sarcin, restrictocin, and mitogillin, also produce selective inhibition of viral expression in HIVinfected cells. It has also been discovered that the selective inhibitory effects are virus specific, as evidenced by lack of selective inhibition in T cells infected with HTLV-I virus, a related, but distinct human retrovirus.

The selective inhibitory effect in HIV-infected cells may be demonstrated by (a) selective inhibition of viral antigen expression in HIV-infected mononuclear phagocytic lineage cells; (b) selective inhibition of cellular proliferation, as measured against protein and DNA synthesis levels in treated, noninfected T cells; and (c) selective loss of T cell viability. These inhibitory effects have been observed for several representative single-chain plant and fungal ribosome inactivating proteins (scRIPs).

It has further been found that the selective inhibitory effects in HIV-infected cells can be achieved by continuous cell exposure to the scRIP, at a selected scRIP concentration, or by short-term or pulsed exposure, e.g., 30–120 minutes, of HIV-infected cells to the scRIP. In the pulse-exposure approach, the concentration of scRIP and time of exposure can be selected to produce nearly complete inhibition of HIV-infected T cells, without appreciable inhibition in noninfected cells.

In one aspect the method of the invention includes exposing HIV-infected T cells and mononuclear phagocytic lineage cells to a single-chain ribosome inactivating protein (scRIP), at a concentration and duration of exposure which are effective to produce a substantial reduction in viral antigen expression in the cells. Since the inhibitory effect of the scRIPs in mononuclear phagocytic lineage cells is selective for viral antigen expression, the scRIP dose/exposure time can be selected to produce inhibition of viral protein expression in HIV-infected cells, with substantially less inhibition of cellular protein synthesis in the HIV-infected cells. Alternatively, since the scRIPs are selectively inhibitory of cellular proliferation in HIV-infected T cells, the scRIP dose/exposure time can be selected to produce inhibition of cell proliferation in HIV-infected T cells, as measured, for example, by selective loss of cell viability in the HIV-infected cells, or by inhibition of thymidine uptake in the cells, without significantly inhibiting these parameters in uninfected T cells. Typically, the concentration of anti-HIV protein to which the cells are exposed is between about 0.01 and 1 ug/ml.

The ability of the scRIPs to inhibit HIV antigen expression in infected cells is exploited, according to another aspect of the invention, for treating HIV infection in humans. The method includes administering a single-chain ribosome inactivating protein to the subject, at a dose which is effective to produce a measurable decrease in at least one of the following indications of HIV infection:

(a) HIV antigen levels associated with HIVinfected T cells or mononuclear phagocytic lineage cells;

(b) HIV antigen levels in the bloodstream;

(c) the reverse transcriptase activity associated with HIV-infected T cells or mononuclear phagocytic lineage cells;

(d) the ratio of viability of HIV-infected to uninfected T cells; and (e) the ratio of a selected HIV antigen to a selected cellular antigen in HIV-infected mononuclear phagocytic lineage cells.

The decrease in indication(s) is preferably measurable within 1–5 days after protein administration. The method may additionally include alternatively measuring the decrease in at least one of the indications, and repeating the protein administration, until the measured indication of HIV infection shows no further decrease.

Preferred scRIPs include plant-derived and fungal-derived scRIPs, such as trichosanthin, momorcharin, pokeweed antiviral protein, alpha-sarcin, mitogillin, and restrictocin.

These and other objects and features of the invention will become more fully apparent when the following detailed description of the invention is read in conjunction with the accompanying drawings, wherein:

BRIEF DESCRIPTION OF THE DRAWINGS

FIGS. 1A–1C show chromatography elution profiles obtained in the isolation of trichosanthin;

FIGS. 2A–2C show chromatography elution profiles obtained in the isolation of alpha and beta momorcharin;

FIGS. 3A–3H are cytofluorographic plots (linear scale) of T cells reacted first with control (nonspecific) antibody (frames at the left) or human anti-HIV antibody (frames at the right) followed by fluorescein-labeled anti-human antibody for uninfected T cells (3A,B); HIV-infected T cells (3C,D); and uninfected or HIV-infected T cells 16 days after exposure to 10 ug/ml TCS (3E,F) or MMC (3G,H).

FIG. 4 shows percent inhibition of p24 HIV antigen expression in HIV-infected T cells as a function of concentration of TCS (open and closed squares) and MMC (triangles);

FIG. 5 shows percent inhibition of p24 HIV antigen expression in HIV-infected T cells as a function of concentration of PAP-I (open squares), PAP-II (triangles), and PAP-S (closed squares);

FIG. 6 shows percent inhibition of p24 HIV antigen expression in HIV-infected T cells as a function of concentration of mitogillin (open squares), restrictocin (triangles), and alpha-sarcin (closed squares);

FIG. 7 shows the decrease in HIV replication in infected cells treated with TCS and MMC, as evidenced by decreased levels of particle associated reverse transcriptase (RT) detectable in the culture supernatant harvested 5 days after addition of TCS (solid diamonds) or MMC (open squares), where the solid squares indicate lack of RT activity in uninfected cells;

FIGS. 8A and 8B are cytofluorographs of permeabilized uninfected (8A) and HIV-infected (8B) monocyte/macrophages after labeling with mouse anti-p24 antibody and fluorescein-tagged anti-mouse antibody;

FIG. 9 shows the increase in percent macrophages containing expressed viral p24 antigen as detectable by permeabilized fluorescence analysis), as a function of time after in vitro infection with HIV, in normal macrophages derived from each of two donors (open circles and triangles), and the change in cell viability which occurs in the cells during the same period (closed circles and triangles);

FIGS. 10A–10D are cytofluorographs of uninfected (10A) and HIV-infected (10B) monocyte/macrophages, and infected macrophages treated with 5 ug/ml of TCS (10C) or 5 ug/ml MMC (10D) four days prior to assaying for the presence of p24 viral antigen, as in FIG. 8;

FIG. 11 is a plot showing the increase in HIV p24 antigen expression during a 10-day period after monocyte/macrophages isolated from an HIV-infected patient are first placed in culture (open squares), and the inhibition of p24 expression when the cells are exposed to 0.3 ug/ml TCS when the cells are first placed in culture (closed circles) or when TCS (0.3 ug/ml) is added after 4 days in culture (closed squares), when a large proportion of the cultured cells are already expressing p24 antigen;

FIG. 12 is a plot showing the change in percent of HIV-infected monocyte/macrophage cells with detectable levels of HIV p24 antigen (as detectable by permeabilized fluorescence analysis), as measured at 0, 24, and 96 hours after exposure of the infected cultures to 5 ug/ml of TCS (closed triangles), MMC (open circles), or no drug treatment (solid circles);

FIG. 13 is a plot showing the change in percent of HIV-infected monocyte/macrophage cells with detectable levels of HIV p24 antigen, measured as in FIG. 8 four days after exposure to 0, 0.5 or 5 ug/ml of TCS (open triangles) or MMC (open circles);

FIG. 14 shows the percent of p24 antigen expression, with respect to untreated cells (100%), four days after exposure to 0, 0.005, 0.05, 0.5, and 5 ug/ml MMC (triangles);

FIG. 15 shows the extent of inhibition of cellular proliferation, as measured by percent $^3$H-hymidine incorporation into cellular DNA in HIV-infected T cells (H9.HIV) and uninfected cells (H9), expressed as a function of TCS concentration;

FIGS. 16A and 16B show the extent of inhibition of cellular proliferatioh, as measured by percent $^3$H-thymidine incorporation into cellular DNA in HIV-infected T cells (H9.HIV) and uninfected cells (H9), as a function of time of exposure to TCS (16A) or MMC (16B) at 2 ug/ml;

FIGS. 17A and 17B are plots showing the absolute viable cell counts for identically seeded cultures of HIV infected (H9.HIV) and uninfected (H9) T cells cultured in the presence of varying concentrations of TCS for 2 days (FIG. 17A) or 5 days (FIG. 17B), and FIG. 17C shows the percentage of viable cells present after 2 days in identically seeded cultures treated with varying concentrations of TCS;

Figure 22:
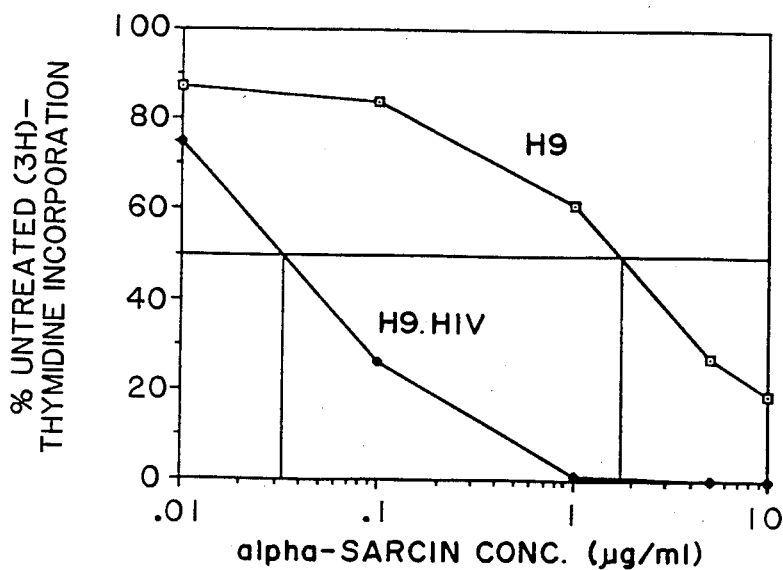
Figure 23A:
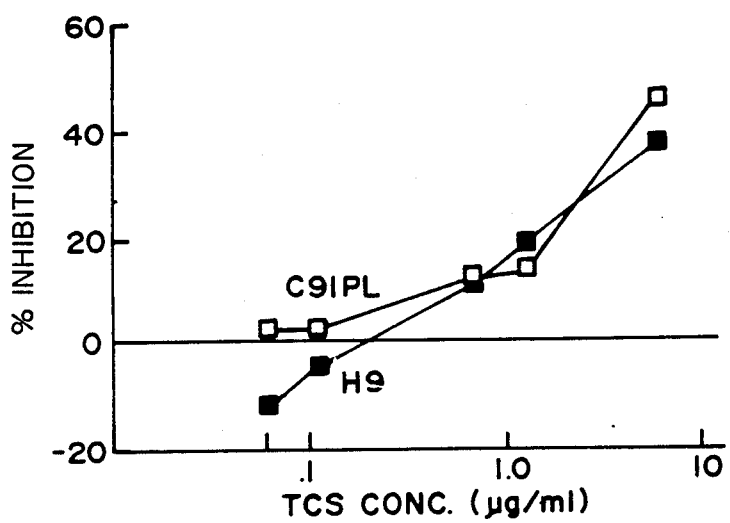
Figure 23B:
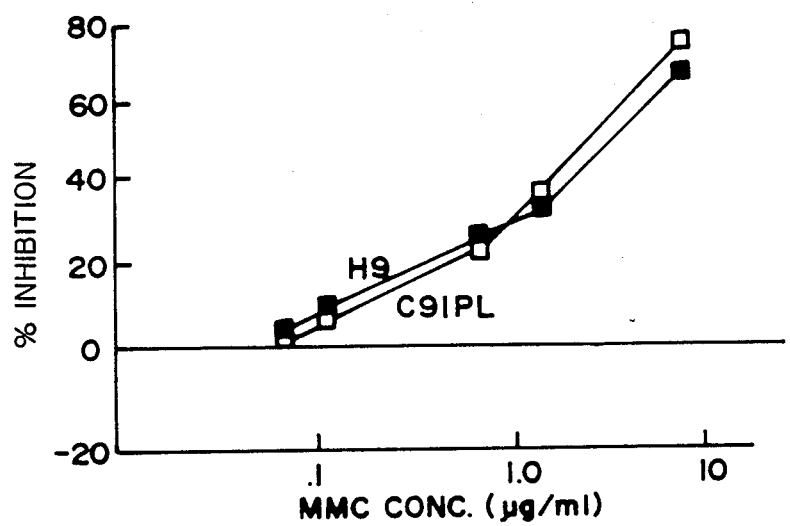
Figure 23C:
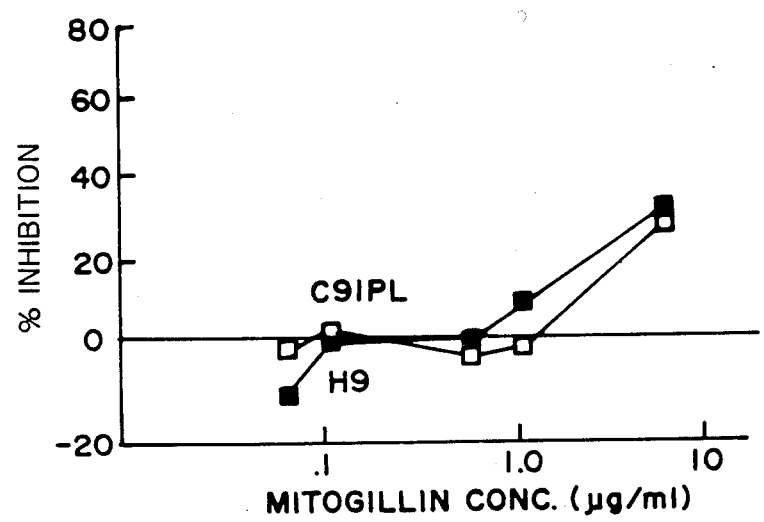

FIG. 22 shows the extent of inhibition of cellular proliferation, as measured by percent $^3$H-thymidine incorporation into cellular DNA in HIV-infected T cells (H9.HIV) and uninfected cells (H9), as a function of alpha-sarcin concentration; and FIGS. 23A-23C shows percent inhibition of cellular proliferation, as measured by percent $^3$H-thymidine incorporation into cellular DNA in HTLV-I-infected T cells (open squares) and uninfected T cells (closed squares), measured at increasing concentrations of TCS (23A), MMC (23B), and mitogillin (23C).

DETAILED DESCRIPTION OF THE INVENTION

I. Definitions

The terms below have the following meanings herein, unless indicated otherwise:
1. "HIV" means a CD4+-dependent (T4, leu3-dependent) human immunodeficiency retrovirus as exemplified by HIV-1 and known variants thereof.
2. "Mononuclear phagocytic lineage cells" means CD4+ mononuclear phagocytes, including CD4+ peripheral blood monocytes, peritoneal macrophages, Langerhans cells of the skin, dendritic reticulum cells of the lymph nodes, pulmonary macrophages, Kupfer cells of the liver, and monocyte/macrophage cells.
3. "Monocyte/macrophage cells" are mononuclear phagocyte lineage cells present in peripheral blood which are precursors of blood macrophages. The cells are obtained from peripheral blood or human spleen biopsies and cultured in cell culture.
4. "T cells" means either transformed T lymphoid cell lines susceptible to HIV infection, or HIV-susceptible T cells derived from primary, peripheral blood mononucleate cell preparations.
5. "HIV-infected cells" means HIV-infected T cells and/or mononuclear phagocytic lineage cells.
6. "Uninfected cells" means T cells and/or mononuclear phagocytic lineage cells which are not infected with HIV.
7. "Single-chain ribosome inactivating proteins (scRIP)" refer to single-chain proteins or peptides capable of inhibiting protein synthesis in a cell-free protein synthesizing system, by site-specific enzymatic inactivation of eukaryotic ribosomal RNA as described in Section IV below.

II. Selective Inhibition of HIV Antigen Expression

This section examines the parameters of selective inhibition of HIV antigen expression in HIV-infected human cells by scRIPs. The human cells which are specifically described are T cells, whose destruction in vivo is associated with loss of immunological function in advanced clinical HIV infection; and monocyte/macrophages, a type of mononuclear phagocytic lineage cell, as defined above, which are likely provide a reservoir of the virus in the infected individual, and may, when expressing HIV proteins, be capable of fusing with and destroying T cells. The monocyte/macrophages may also play a role in the spread of the infection, particularly as within the nervous system (Koenig).

A. T Lymphocyte Cells

Normal human T lymphocytes can be prepared from peripheral blood or from lymphoid solid tissue by standard procedures (Foung). The cells include a fraction of CD4+ cells which may be further isolated, if desired, by affinity methods which are specific for the CD4+ surface antigen. In the usual case, the mixture of CD4+ and nonCD4+ cells are employed. The cells are maintained in culture over a several-day to several-week period by activation with a known lymphocyte mitogen, such as PHA, and in standard cell media, such as RPMI-1640 medium supplemented with fetal calf serum and interleukin-2. The cultured T lymphocytes may be infected with HIV in vitro, e.g., using an HIV isolate derived from an AIDS patient.

In addition, continuous T cell lines, typically derived from patients with lymphoid malignancies, may also be employed. Such cells may be maintained in standard cell culture media, such as RPMI 1640 supplemented with heat-inactivated fetal calf serum.

One characteristic of HIV-infected T cells is the appearance of HIV envelope proteins, particularly the major envelope proteins gp120 and gp41, on the surface of the infected cells. As indicated above, gp120 appears to play a critical role in the recognition of CD4+ T lymphocytes, cytes, and the subsequent destruction of these lymphocytes. gp41may also participate in HIV envelope mediated cell fusion (Kennedy). Therefore, the ability of the scRIPs herein to inhibit expression of these viral antigens may be an important indicator of the ability of the protein to inhibit virally mediated processes leading to T cell destruction and to arrest the loss of immunological function seen in HIV-related diseases, such as AIDS. The demonstrated antiviral properties are not, however, limited to action via this mechanism.

The effects of TCS and alpha-MMC on the expression of HIV antigens (including gp120 and gp41) on the surface of infected T cells were examined, as detailed in Example 3. The effect of continuous TCS and MMC exposure on HIV antigen expression are shown in FIG. 3. HIV infected T cells (H9 cell line) were treated with 10 ug/ml of TCS or alpha-MMC for 16 days, then tested for HIV antigen expression by indirect immunofluorescence analysis. Briefly, human serum from an HIV-positive individual was incubated with test cells, followed by washing and detection of bound specific IgG with a fluoresceinated goat anti-human IgG reagent. The results of the quantitative flow cytometry analysis are shown in FIG. 3, and discussed in Example 3. The results show that both TCS and MMC reduced the level of HIV antigen expression in treated, HIV-infected T cells to background levels.

Figure 12:
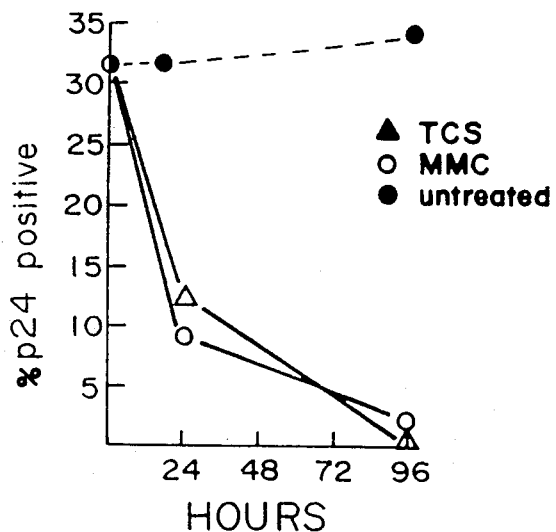

Another HIV antigen which can be used as an indicator of HIV antigen expression in HIV-infected T cells is the HIV core protein antigen p24. This antigen, which is localized predominantly within the infected cells, can be measured readily by treating the cells with a membrane-permeabilizing agent, such as Triton X-100 TM, to facilitate entry of anti-p24 mouse monoclonal into the cells, then treating the cells with a fluorescent-tagged anti-mouse IgG antibody. These methods are detailed in Example 4. Alternatively, viral replication may be quantified by determining the amount of HIV p24 antigen present in either cell-free supernatants of infected cultures or in lysates of infected cells, through use of a sandwich type antigen-capture immunoassay. Both approaches provide a measure of viral antigen expression or production, i.e., the amount of HIV antigen produced by the infected cells and detectable by the particular assay means used.

The effect of low concentrations of several scRIPs on p24 expression in HIV-infected T cells was examined, according to procedures detailed in Example 4. Briefly, HIV-infected and noninfected T cells were cultured with the selected scRIP, at continuous-exposure concentrations of between 0.01 and 5 ug/ml, for 10 days, then assayed for p24 antigen as above. FIG. 4 shows the percent inhibition of p24 produced by the indicated TCS and MMC concentrations. The data indicate substantially complete inhibition of viral antigen at scRIP continuousexposure concentrations of 1 ug/ml.

FIG. 5 shows the effect of three pokeweed antiviral protein preparations on p24 expression in HIV-infected T cells. The results are qualitatively similar to those produced by TCS and MMC, although slightly higher scRIP concentrations were required to produce complete inhibition of p24 expression.

In FIG. 6, the inhibitory effect of three fungal scRIPs on p24 expression in HIV-infected cells is shown. As seen, the lowest concentrations tested produced complete or nearly complete inhibition of p24 expression in infected T cells. The apparently greater specific activity of the fungal scRIPs may be due in part to their lower molecular weights (Section I), and thus greater molar concentration at the indicated ug/ml concentration levels.

It has been confirmed that the inhibition of HIV antigen expression discussed above represents an inhibition of viral replication, as indicated by a loss of reverse transcriptase (RT) activity in the infected cells. This feature is seen in FIG. 7, which plots the reverse transcriptase activity in HIV-infected T cells, as a function of TCS or MMC concentration. The fall in RT activity correlates well with inhibition in HIV surface antigen expression in infected cells (FIG. 3).

As will be seen in Section III below, the 0.1–1 ug/ml concentrations of scRIP required to produce substantially complete inhibition of HIV antigen expression in infected T cells produces little if any inhibition of cellular proliferation in noninfected T cells. This selectivity effect in T cells can thus be exploited to inhibit HIV infection in infected T cells, with little toxic effect on uninfected cells.

B. Mononuclear Phagocytic Lineage Cells

Since mononuclear phagocytic lineage cells (MPLC) represent another group of HIV infectable cells, and probably provide a significant reservoir of the virus in humans, the inhibitory effect of scRIPs against HIV infection in this cell group is also of interest. The cell type which has been examined is the monocyte/macrophage, a mononuclear macrophage-lineage cell present in the peripheral blood, and a precursor of tissue macrophages. These cells, which will be referred to herein for simplicity as "monocytes", can be isolated from peripheral blood or from human spleen biopsies by known procedures (Crowe). The cells are preferably cultured in a novel in vitro culture system which employs Teflon ® coated culture vessels, as described in Example 6. Upon in vitro culture, peripheral blood derived monocytes undergo differentiation, acquiring some characteristics of tissue macrophages. For isolation of monocytes, peripheral blood mononuclear cells are allowed to attach to a glass dish, permitting separation of the monocytes from non-adherent lymphocytes. The separated monocytes are then cultured as a suspension on Teflon ®-coated dishes. Although the cells do not proliferate, they can be maintained in a viable state in culture for up to four months or more without significant loss of cell viability.

The cells can be infected in vitro with an HIV isolate, as described in Example 6, or obtained in infected form from an HIV-infected individual, by similar methods. HIV antigen expression in monocyte/macrophages can be readily followed by changes in p24 antigen, as outlined above. FIGS. 8A and 8B show cytofluorographs of HIV-infected monocytes reacted with control (non-specific) or mouse anti-p24 antibodies, respectively, measured 10 days after HIV infection in vitro. About 60% of the cells have detectable (above background) fluorescence levels, indicating HIV infection.

One important feature of the monocyte cell culture system, for studying HIV infection and inhibitors, is that the cells can be maintained in an actively infected state in culture for extended periods of several weeks or more. This feature is seen in FIG. 9, which plots monocyte viability (closed symbols) and p24 antigen levels (open symbols) as a function of days after infection in vitro with HIV, where the circles and triangles represent two different monocyte donors. Experimental details are given in Example 6. As seen, viral antigen increases steadily to a maximum of about 50–60% infected cells, then plateaus after about two weeks, while cell viability remains substantially unchanged over the test period.

The inhibition of viral antigen expression in HIV-infected monocytes, when exposed to TCS or MMC, is illustrated in FIG. 9. Here, monocytes were exposed to 5 ug/ml TCS or MMC ten days after HIV infection, and four days later, the cells were assayed by flow cytometry. FIGS. 10A and 10B show the cytofluorographs of untreated cells analyzed after reaction with control (non-specific) and anti-p24 antibody, similar to FIGS. 8A and 8B, respectively. The cytofluorographs of TCS- and MMC-treated cells are shown in FIGS. 10C and 10D, respectively. The level of p24 seen in the scRIP-treated cells (FIGS. 10C, 10D) is close to background (FIG. 10A), indicating substantially complete inhibition of viral antigen expression four days after cell exposure to anti-viral proteins. Example 7A gives details of the method.

The time course of loss of p24 antigen in infected monocytes after exposure to TCS or MMC is seen in FIG. 12. Each time point represents percent cells with an above-background antigen-specific fluorescence, determined as above by flow cytometry. Untreated cells (solid circles) show little change in antigen levels, whereas both TCS (triangles) and MMC (open circles) treated cells show a severalfold reduction in viral antigens 1 day after, and substantially complete loss of p24 antigen 4 days after exposure to TCS or MMC. Details of the study are given in Example 7B.

Figure 13:
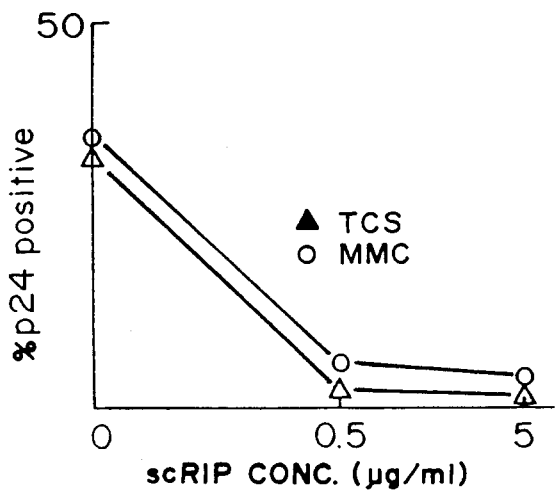
Figure 14:
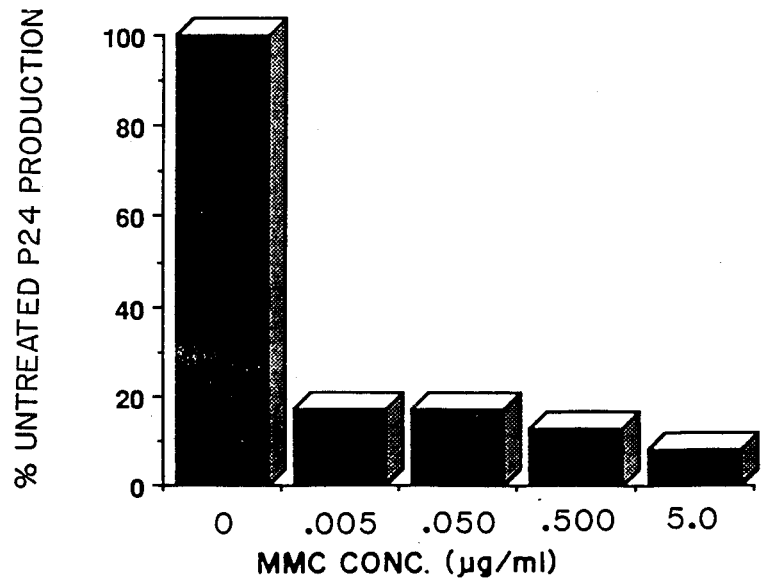

The data in FIG. 13, which plot the inhibition in p24 expression as a function of TCS or MMC, show that both TCS and MMC produce nearly complete inhibition of p24 expression at a concentration of 0.5 ug/ml. In FIG. 14, the percent inhibition of p24 with 3 hour pulse exposure to MMC, at concentrations as low as 0.005 ug/ml, is seen. The data show nearly complete inhibition at 5 mg/ml concentration.

According to another aspect of the invention, it has been found that the inhibitory effect of scRIP on HIV-infected monocytes is selective for viral proteins, at least when the infected cells are given a pulse exposure to a low dose of the scRIP. Specifically, it has been found that HIV-infected monocytes, when exposed to a low-concentration pulse dose of scRIP, show a marked reduction in measurable p24 (FIG. 14), but no significant reduction in measurable cellular surface antigens, as exemplified by the surface antigen HLA-DR. Details of the study are provided in Example 7D.

Figure 7:
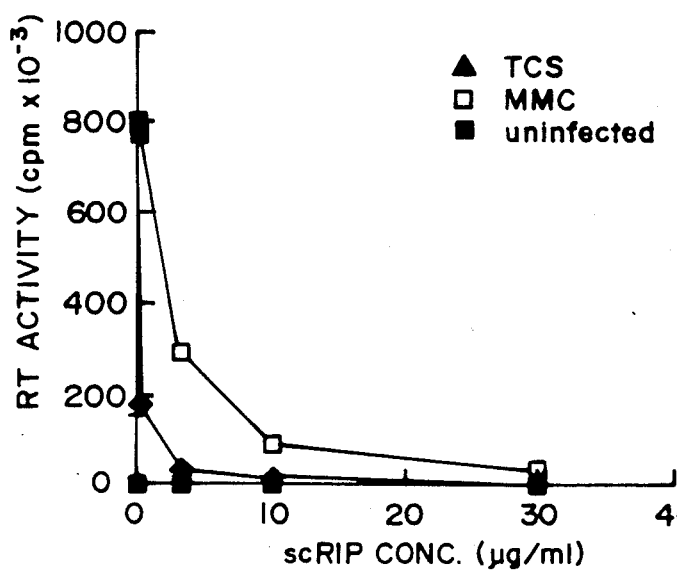
Figure 8A:
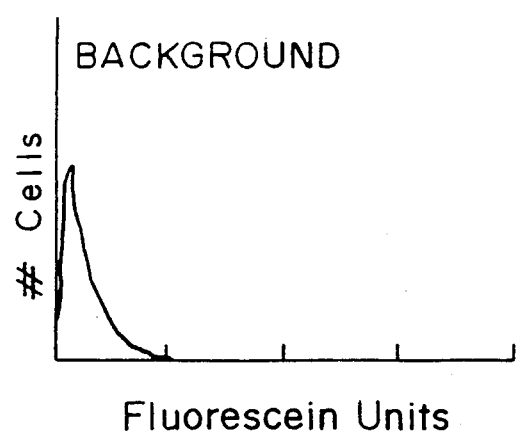
Figure 8B:
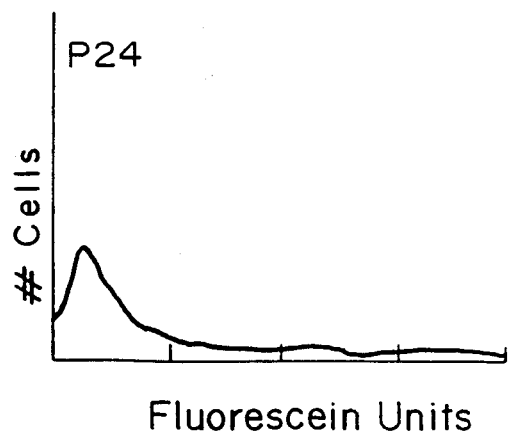
Figure 9:
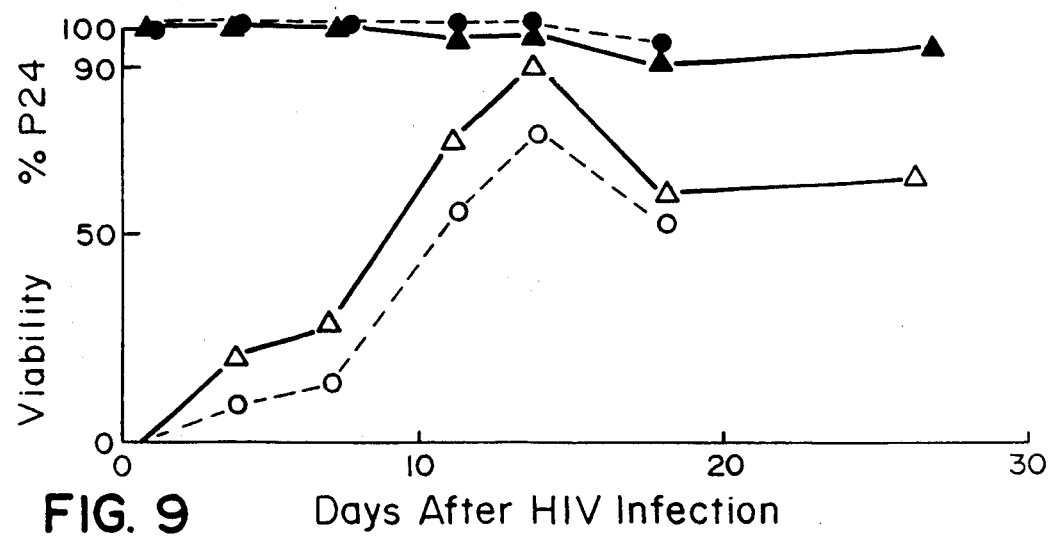
Figure 10A:
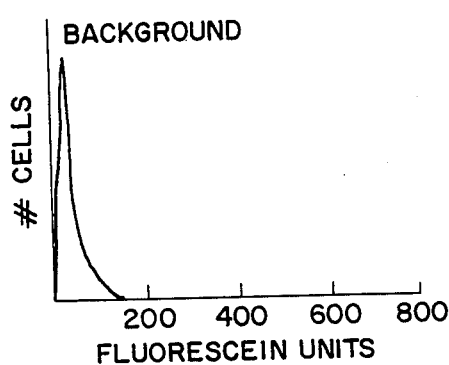
Figure 10C:
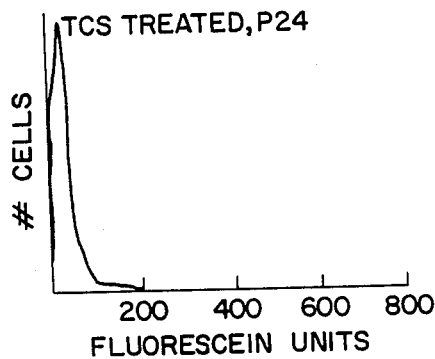
Figure 10B:
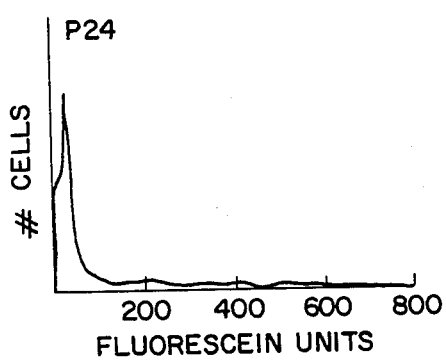
Figure 10D:
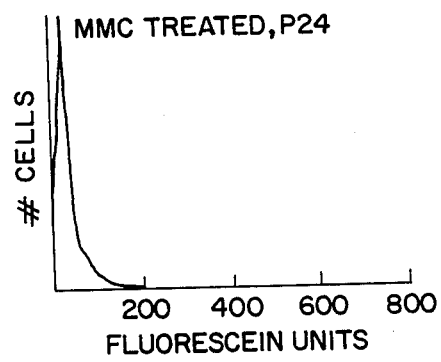

The presence of HIV in macrophages isolated from AIDS patients, and the inhibition of HIV antigen expression in monocytes infected in vivo and isolated from a infected donor was also examined. Several monocyte preparations from both peripheral blood and spleen cells from AIDS patients were tested for p24 antigen expression. The macrophage cultures were established essentially as described in Example 4, except that the donors were HIV seropositive, and no exogenous virus was added to accomplish in vitro infection. The source of HIV in the culture was that present from natural, in vivo infection of the cell donor. Monocytes tested immediately after isolation contained only a small percentage of HIV positive cells, as evidenced by the presence of p24 antigen. The percentage of cells expressing p24 increased gradually over a 3 to 4 day period in culture, as indicated for a culture of spleen monocytes (open squares) in FIG. 11. In five different monocyte preparations derived from HIV-seropositive individuals which have been examined, the cultured cells expressed between about 10%40% p24 after 3-4 days in culture. The results indicate that a high proportion of monocytes present in HIV seropositive individuals are infected with HIV. Apparently only a small percentage of those infected cells express HIV antigens unless cultured for short periods in vitro. The possibility that the increase in number of cells expressing p24 is caused by the spread of the virus among the cultured cells is unlikely, given the relatively slow rate of p24 expression in newly-infected cultured monocytes (FIG. 7).

Figure 11:
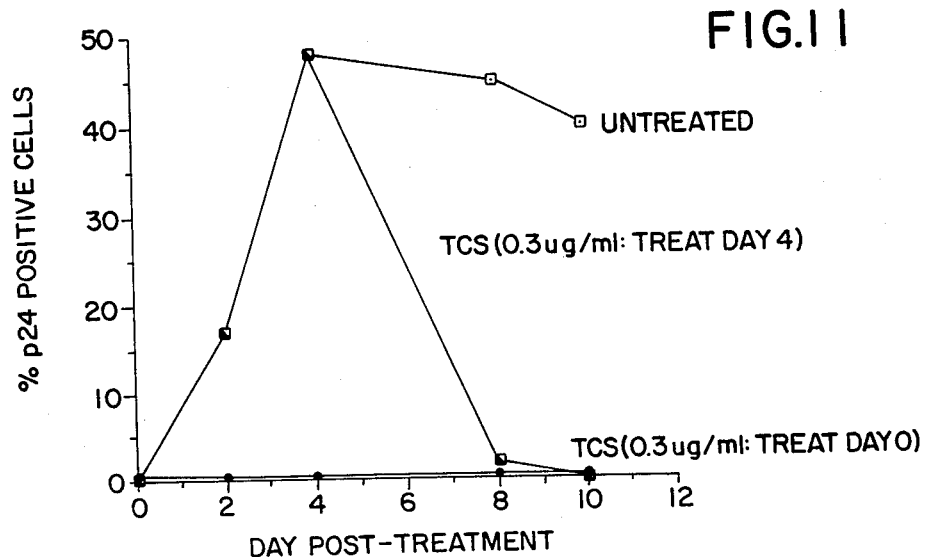

The inhibitory effect of TCS on p24 expression in the in vivo infected cells was examined both at the initiation of the culture, when the percentage of p24 expressing cells was quite low and, in a separate culture, 5 days after initiation of culture, at which time p24 expression was observed in about 45% of the cells. FIG. 11 shows the results of TCS treatment (0.3 ug/ml) of $5 \times 10^5$ monocytes cultured over a ten day period. TCS added at the initiation of the culture completely prevented HIV antigen expression over the 10-day test period. When added to the 5-day monocyte culture, TCS reduced the percentage of cells expressing p24 from about 45% to 2% within three days, and further reduced the percent of antigen-expressing cells to background level within 5 days. It is clear from the data that TCS can block HIV antigen expression in monocytes derived from an infected individual, either before or after antigen expression occurs in culture.

The methods and findings which are discussed herein can be summarized as follows:

1. Initial findings, presented in the copending patent application for "Method of Inhibiting HIV" demonstrated that low concentrations of TCS and alpha- and beta-MMC effectively inhibit HIV antigen expression in HIV-infected T cells and mononuclear macrophage lineage cells. Low concentrations (e.g., less than about 1 ug/ml) of the same compounds gave only slight inhibition of protein synthesis in non-infected cells.

2. The above selective inhibitory effects on viral expression in infected T cells and monocyte/macrophages have now been demonstrated for several additional single-chain ribosome inactivating proteins, including scRIPs from both plant and fungal sources.

3. In addition to the selective inhibitory effects seen in HIV-infected T cells and monocyte/macrophages (as evidenced by the lack of protein inhibition produced in non-infected cells at low scRIP concentrations), scRIP are capable, at low concentrations and/or low exposure times, of selectively inhibiting viral protein synthesis in HIV-infected monocyte/macrophages.

III. Selective Inhibition of T Cell Proliferation

Studies presented in the earlier-filed copending patent application showed that TCS, gave a marked selective reduction in cell proliferation and viability in HIV-infected cells. This section examines the parameters of selective inhibition of cellular proliferation in HIV-infected cells. The selective inhibitory effect of several representative scRIPs on cell proliferation, at low dose levels, has now been established. In addition, it has been found that essentially complete selectivity can be achieved by pulse dosing. It is also shown that the selective effects are relatively specific for HIV infection, since no appreciable selective inhibitory effects are observed in T cells infected with a related, but distinct human retrovirus, HTLV-I.

Inhibition of cellular proliferation was determined by following the inhibition of thymidine uptake in treated cells, and in some cases, this approach was supplemented with data on inhibition of amino acid uptake and/or reduction in cell viability. Details of the cellular lular inhibition studies are given in Examples 8 and 9.

Figure 15:
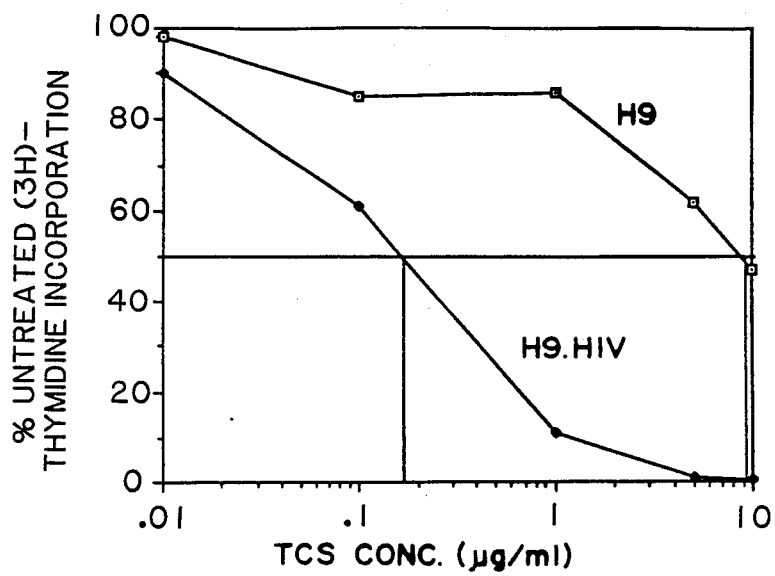

To determine effective inhibitory dose of scRIP, the noninfected and HIV-infected cells were exposed to increasing quantities of the selected scRIP, typically at concentrations between 0.01 and 5 ug/ml, and over an exposure period of three days. The cells were then pulsed with radiolabeled thymidine for 12 hours and radiolabel incorporated into cellular DNA was measured, as an index of cellular proliferation. FIG. 15 shows the levels of thymidine incorporation measured at 0.01, 0.1, 1, 5, and 10 ug/ml TCS, where H9 and H9.HIV indicate noninfected and HIV-infected T cells, respectively. As seen, 50 percent inhibition of infected cells is achieved at about 0.2 ug/ml, whereas the same degree of inhibition in noninfected cells requires nearly 10 ug/ml TCS. The selectivity index, defined as the ratio of the two concentrations, is thus about 50 for TCS. Similar results (not shown) have been obtained for MMC.

Figure 16A:
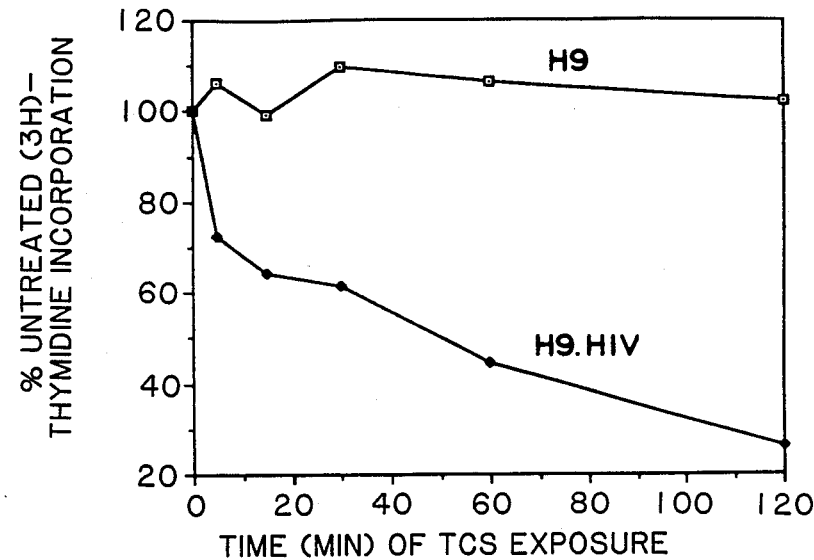
Figure 16B:
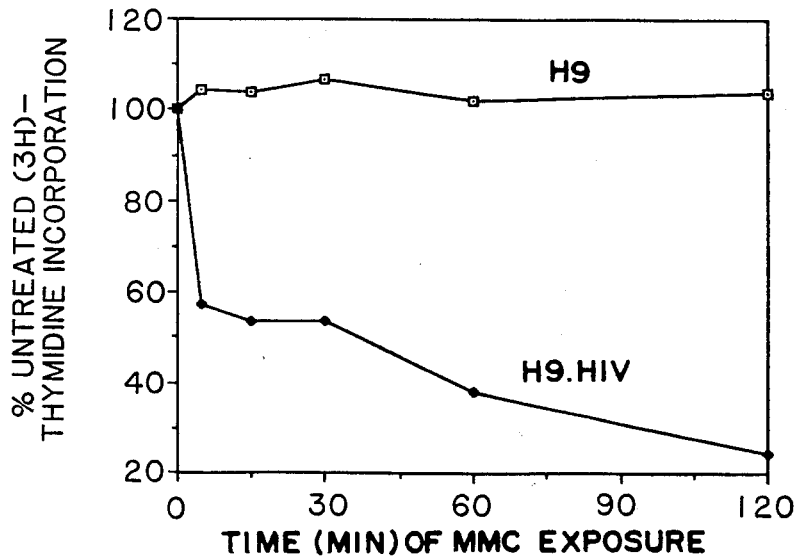

As seen from FIG. 15, the maximum selectivity effect (greatest difference between the two curves) was observed at 1 ug/ml TCS. According to one aspect of the invention, it has been discovered that the selectivity of inhibition between infected and noninfected cells can be enhanced substantially by exposing the cells to a pulse dose of the selected scRIP, as distinguished from continuous exposure. This effect is seen in FIGS. 16A and 16B, which show the inhibition of thymidine uptake as a function of exposure time to 2 ug/ml TCS (16A) or MMC (16B). As shown, neither scRIP tested gave appreciable inhibition of thymidine uptake by noninfected cells after exposure to the compounds for up to two hours. By contrast, a 2 hour exposure, with no subsequent exposure, was sufficient to produce a nearly complete inhibition of cellular proliferation in the infected cells, when measured three days later.

Figure 17A:
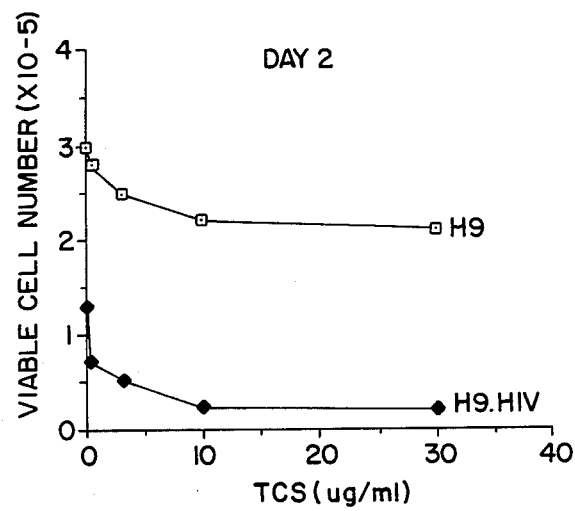
Figure 17B:
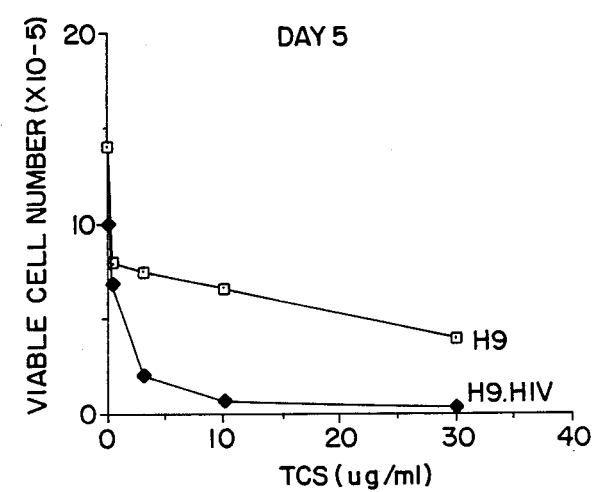
Figure 17C:
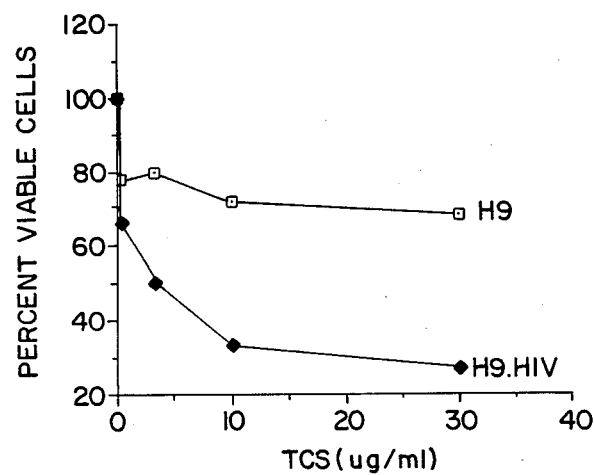

FIGS. 17A-17C show the effect on cell viability of increasing concentrations of TCS, as reported in the earlier-filed patent application. Viable cell numbers, 2 and 5 days following exposure to TCS at the concentration indicated, are plotted in FIGS. 17A and 17B, respectively, and percent viable cells, in FIG. 17C, where cell viability was determined by vital dye exclusion (trypan blue).

The cell viability data in the figures shows that infected cells are more susceptible to killing, particularly at higher concentrations of TCS, with a more pronounced effect observed at 2 days than at 5 days. This likely reflects the fact that less than one hundred percent of the cells within the "infected" population were actually productively infected. Cells which are not productively infected appear to be less susceptible to TCS and MMC; the apparent relatively lesser effect of drug exposure on cell counts at day 5 may reflect preferential outgrowth of individual cells within the "infected" population which were not themselves productively infected. Comparison of total viable cell numbers with percentage viability suggests that TCS, in a dose-dependent fashion, can exert both cytocidal (cell killing) and cytostatic (cell growth inhibiting) effects, with preferential effects at a given peptide concentration on HIV infected cells relative to uninfected cells. Similar results were obtained with alpha and beta-MMC.

Figure 18A:
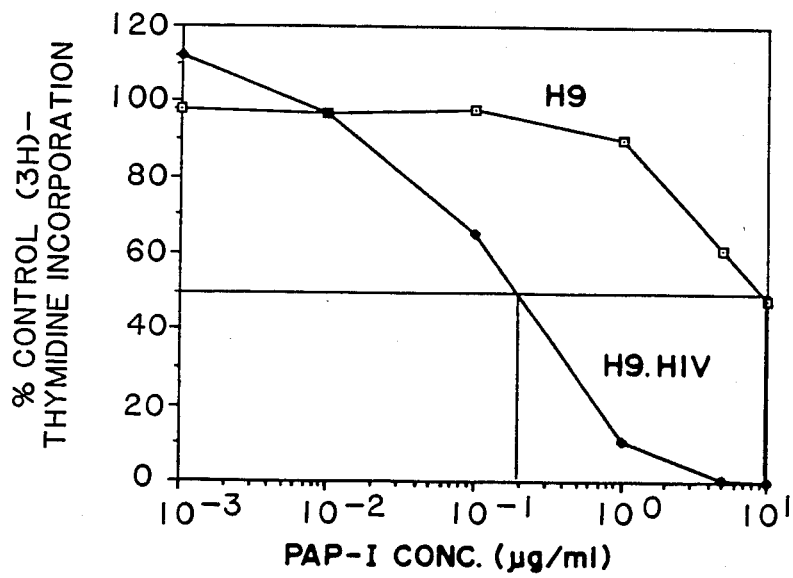
FIGS. 18A and 18B show percent inhibition of cellular proliferation of HIV-infected (H9.HIV) and non-infected (H9) T cells with exposure to increasing concentrations of PAP-I, as evidenced by inhibition of $^3$H-thymidine incorporation into cellular DNA (18A), and inhibition of $^3$H-leucine incorporation into cellular protein (18B)
Figure 18B:
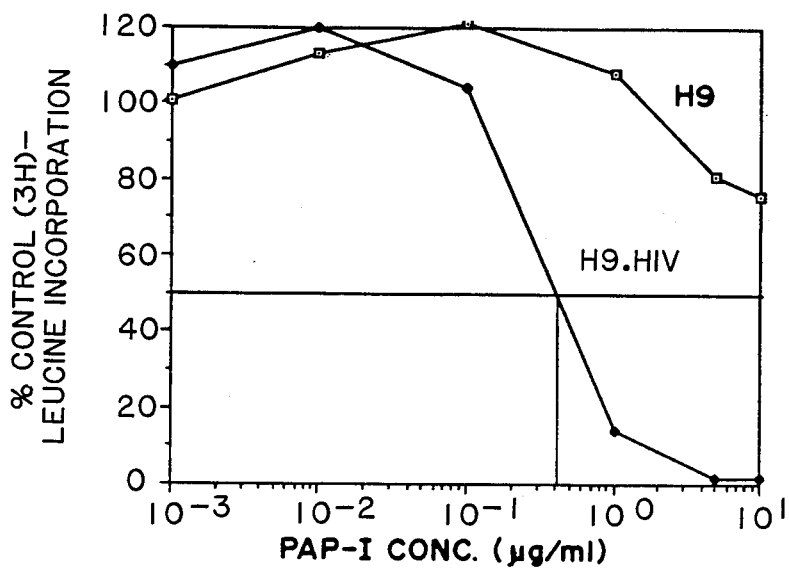

FIGS. 18A and 18B show the degree of cellular inhibition of H9 and H9.HIV cells with exposure to increasing concentrations of PAP-I. As seen in FIG. 18A, the 50 percent inhibitory levels and selectivity index for thymidine incorporation are very similar to those seen for TCS. FIG. 18B demonstrates that the inhibition of amino acid (leucine) incorporation into treated H9 and H9.HIV cells closely follows the inhibition of thymidine uptake.

FIGS. 19-22 show selective inhibition curves for H9 and H9.HIV cells treated with PAP-II (FIG. 19), mitogillin (FIG. 20), restrictocin (FIG. 21), and alpha-sarcin (FIG. 22). In all cases, the selectivity index was between about 50-70. Consistent with the viral antigen inhibition data discussed in Section III above, the data here indicate that the three fungal proteins tested are inhibitory at concentrations somewhat lower than observed with plant scRIPs.

The inhibitory effect of scRIPs on T cells infected with HTLV-I was also examined. HTLV-I (human T-cell leukemia/lymphoma virus) has several features in common with HIV, including a tropism for OKT4+/leu3+ lymphocytes, cytes, a $Mg^{+2}$-dependent high molecular weight reverse transcriptase, similar size and nature of some structural proteins, and limited nucleic acid homology (Sarngadharan).

T cells infected with HTLV-I were exposed to increasing concentrations of TCS, MMC, or mitogillin, according to methods described in Example 10. The inhibition of thymidine incorporation, as a function of scRIP concentration, for both noninfected (H9) and infected (C9/PL) T cells is shown in FIGS. 23A-23C, for the three proteins tested. No selective inhibition was observed with any of the tested compounds. Specifically, HTLV-I infected cells were no more susceptible to inhibition by the compounds than noninfected H9 cells.

The methods and findings which are discussed herein can be summarized as follows:

1. Initial findings, presented in the copending patent application for "Method of Inhibiting HIV" demonstrated that TCS and MMC can selectively inhibit cellular proliferation in HIV-infected T cells, as evidenced both by inhibition of thymidine uptake and reduced cellular viability.

2. The selective inhibitory effects on cellular proliferation in infected T cells have now been demonstrated for several additional A-chain like plant and fungal proteins. All of the tested compounds show a selectivity index of between about 50-70 when tested under assay conditions involving continuous exposure of HIV-infected or uninfected cells to the compounds.

3. By pulse dosing infected T cells with the scRIPs, essentially complete selectivity (i.e., no measurable inhibitory effects on noninfected cells) can be achieved.

4. The selectivity effects are specific for HIV, as evidenced by the lack of any selectivity in T cells infected with a related, but different human retrovirus, HTLV-1.

IV. Single-Chain Ribosome-Inactivating Proteins

The scRIP proteins which are useful in the present invention can be classed generally into one of four groups, depending on source of the protein (plant, fungal, or bacterial) and subunit structure of the naturally occurring protein (single-chain or two-subunit).

The first group includes single-chain inhibitors of protein synthesis which are produced by a large number of plants. Examples of proteins in this group are TCS (Law, Kuo-Fen, Gu, Xuejun, Wang, Kezhen), MMC (Falasca, Spreafico, Lin, 1970, 1978, Barbieri, 1979, 1980), the pokeweed antiviral proteins (Barbieri, 1982, Irvin, 1975, 1980, 1983), gelonin (Stirpe, 1980), dianthin 30 and dianthin 32 (Stirpe, 1981), crotin II (Conde), curcin II (Conde), wheat germ inhibitor (Roberts), and several other protein inhibitors obtained from grains (Coleman, Gasperi-Campani).

A second group of scRIPs are obtained from fungal sources and occur naturally in single-chain peptide form. This group is exemplified by alpha-sarcin (Rodriguez, Olson, 1965a, 1965b), restrictocin (Rodriguez), mitogillin (Rodriguez), enomycin (Conde) and phenomycin (Conde).

Some plants produce cytotoxins which are composed of two dissimilar subunits or peptide chains—an enzymatically active A chain having ribosome inactivating activity specific for the ribosomal RNA of the large ribosome subunit, and a B chain which functions to bind the toxin to cell-surface receptors (Olsnes, 1982). The best-known cytotoxins of this type are ricin, abrin, and modeccin, all of which are similar in structure and mechanism of action. The subunits in these proteins are linked through a disulfide bond, which can be broken under reducing conditions (Olsnes, 1982), allowing purification of the individual subunits. The A subunits of the cytotoxins, i.e., the ribosome inactivating subunits, form the third class of scRIPs, in accordance with the present invention.

The fourth group of scRIPs are single-chain bacterial cytotoxin protein or peptide cytotoxins, such as the cytotoxin from *Shigella dysenteriae*, and related Shiga-like toxins (Calderwood). These toxins are composed of one A chain-like subunit, similar to the A chains of the plant cytotoxins described above and having the identical mode of action (Endo, 1987), and multiple B subunits having cell binding functions. These A subunits form the fourth group of scRIPs.

Several lines of evidence indicate that the scRIPs in all four groups share common structural features and have a common mechanism of action. The A chains of ricin, modeccin, abrin, all show regions of amino acid sequence homology (Olsnes, 1987), and a number of single-chain plant RIPs, including pokeweed antiviral proteins (Irvin, 1975), wheat germ inactivating (Roberts), MMC (Barbieri), gelonin (Stirpe), dianthins (Stirpe), and TCS (Maraganore), resemble the ricin A chain in primary peptide structure. The Shiga-like bacterial toxins also show sequence homology with ricin A (Calderwood). The primary structures of restrictocin, mitogillin, and alphasarcin all show a high degree of sequence homology (Rodriguez).

The scRIPs defined herein also share a common mechanism of ribosome inactivating activity, which involves site specific enzymatic action on the large ribosomal RNA (rRNA) of the 60S ribosomal subunit (Olsnes) In several of the scRIPs which have been investigated, including the A chains of ricin, abrin, and modeccin, the single-chain plant inhibitors pokeweed antiviral proteins, crotin II, curcin II, the fungal proteins mitogillin, alpha-sarcin, restrictosin, eomymic, phenomycin, and Shiga-like bacterial toxins, catalytic inactivation of the 60S subunit of eukaryotic ribosomes has been reported (Conde). In the case of many plant inhibitors, including ricin, abrin, modeccin, and pokeweed antiviral protein, the mechanism of ribosomal inactivation involves an N-glycosidase activity which removes the adenine from a specific adenosine nucleotide subunit. For the fungal inhibitors which have been investigated to date, including alpha-sarcin, mitogillin, and restrictocin, the inactivation event involves phosphodiester cleavage at a specific site close to the cleavage site of the N-glycosidase inhibitors (Endo, 1982, 1987).

Another feature common to single-chain ribosome inactivating proteins which has been reported is enhanced inhibition of protein synthesis in certain virus-infected cell systems. For example, it has been observed that gelonin, dianthin-32, MCI (*M. charantia* inhibitor) and PAP-S all produce a greater inhibition of protein synthesis in HEp-2 cells infected with either herpes simplex virusl (HSV-1) or with poliovirus I than in noninfected cells (Foa-Tomasi) The levels of inhibitor protein required to achieve selective inhibitory effects were typically between 10-100 ug/ml, and the degree of inhibition seen was typically less than about 50% (FIG. 3 of Foa-Tomasi).

More recently, it has been shown that several single-chain inhibitors, including alpha-sarcin, mitogillin, restrictocin, PAP, and the abrin A chain, selectively inhibit protein synthesis in HeLa cells infected by the picornavirus encephalomyocarditis virus (EMC). Selective inhibition was seen at relatively low inactivating concentrations of alpha-sarcin and abrin A chain. Selective inhibition of HeLa cells infected with adenovirus and BHK cells infected with Semliki Forest virus was also observed. Further studies indicated that binding of EMC virus or poliovirus to surface receptors on a virus-infectable host cell may increase the permeability of the cell to inactivating protein (Fernandez-Puentes, 1980, 1983).

Although viral infection may enhance the protein inhibitory effects of single-chain ribosome inactivating proteins on infected cells, this effect appears to depend strongly on the specific virus and infected cell type involved. For example, in the above-mentioned study on virus-infected HeLa cells, infection with EMC showed a substantially greater selective inhibition of protein synthesis than in the same cells infected with adenovirus. In the same reference, BHK cells infected with Simliki Forest virus showed, at most, about a 40% difference in protein inhibition between infected and non-infected cells. And, as indicated above, in HEp-2 cells infected with either poliovirus or HSV-I, selective protein inhibition effects were only observed at high inactivating concentrations, and the maximum difference in degree of inhibition, between infected and non-infected cells, was about 50%.

From the findings presented in Section III above, it is seen that T cells infected with different retroviruses show dramatic differences in their response to scRIPs. In particular, HTLV-I infection of human T cells results in no detectable selective inhibitory action by scRIPs. By contrast, in T cells infected with HIV, a distinct but closely related retrovirus, differences in inhibitory effect of up to 80-90% are observed at low inactivating concentrations of between about 0.1-1 ug/ml concentration. Further, when the cells are exposed to a pulsed dose, differences in selective inhibitory effects up to 100% are observed.

It was earlier shown (copending patent application for "Method of Inhibiting HIV") that low doses of TCS and MMC produced a marked selective inhibition of viral antigen production in HIV-infected T cells and monocyte/macrophages, and a selective reduction in cell viability in infected T cells. This discovery has now been extended to a total of eight scRIPs which are representative of single-chain plant inhibitors and fungal inhibitors. In addition, it has now been shown that the scRIP treatment of HIV-infected T cells and/or monocyte/macrophages produces several important effects which have not been observed heretofore. These are:

(a) Substantially complete inhibition of HIV antigen expression and viral replication in HIV-infected T cells and monocyte/macrophages, at scRIP concentrations which are substantially nontoxic to uninfected cells;

(b) Selective loss of viral antigen with respect to cellular antigen in virus-infected monocyte/macrophages; and (c) Substantially the same degree of selective inhibition produced by a variety of different scRIPs which were tested. In particular, as noted in Section III, all of the plant and fungal compounds tested gave a selectivity index for inhibition of cellular proliferation of between about 50-70. This contrasts with prior art reports where the selectivity effects varied widely among ribosome inactivating proteins which were tested. This result, taken together with the representative nature of the eight scRIP compounds which were tested, indicates that the marked selectivity effects presented herein can be reasonably generalized to include compounds of the four groups of scRIPs defined above.

V. Treating HIV Infection in Humans

One link in the etiology of AIDS appears to be the destruction of CD4+ T lymphocytes, and there is in vitro and in vivo evidence to suggest that at least one mechanism of cell destruction involves fusion of infected cells to form large multi-nucleate cells. The inventors and their coworkers have previously studied the relationship between expression of the CD4 antigen and infectability by HIV (Lifson, 1986a-c). The studies confirmed earlier reports that HIV infection of T lymphocytes requires the CD4 antigen, suggesting that the infection process requires interactions between the CD4 antigen and one or more envelope proteins of HIV (Dalgleish; Klatzman, 1984a, 1984b; McDougal, 1985a, 1985b, 1986; Maddon; Sodroski). The previous study by the inventors also showed that infected T cells can fuse with both infected and non-infected CD4+ T cells in vitro to produce large multi-nucleate syncitia, and that cell fusion can be blocked with addition of anti-CD4 antibodies. This indicates that cell fusion, like HIV infection, requires interactions between viral antigens on the surface of infected cells and the T lymphocyte CD4 antigen (in either infected or non-infected cells). The result may also explain how a large portion of CD4+ T cells can be destroyed in vivo, even though only a relatively small number of isolated CD4+ T cells from an HIV-infected individual show evidence of HIV infection. According to this mechanism, infected T lymphocytes would "recruit" healthy T cells for cell fusion and destruction.

Using T lymphocytes selected for high CD4+ antigen expression, the inventors have further shown in previous studies that (a) the infectability of the T lymphocytes with HIV increases substantially with increased surface concentration of the antigen, and (b) syncytia formation due to cell fusion is much more rapid in the high CD4+ cells. The results support earlier findings on the importance of the CD4+ antigen in HIV infection and subsequent cell-fusion events.

There is also evidence that monocyte/macrophages may be involved the etiology of HIV infection. It has been reported that cells of the monocyte/macrophage lineage can be infected with HIV in vitro (Crowe, Gartner, 1986a, 1986b; Koenig; Ho; Chayt; Armstrong; Steicher), and monocytes have been implicated in the spread of HIV into the central nervous system (Koenig). The studies reported in Section III on monocytes prepared from HIV-infected patients indicate that a large percentage of blood and splenic macrophages may harbor HIV infection, even though viral antigens may be actively expressed in vivo in a relatively small percentage of the cells. In addition to providing a possible reservoir of HIV in the body, macrophages may also be directly involved in the destruction of T lymphocytes by cell fusion. Recent studies by the inventors and their coworkers show that HIV-infected monocytes are capable of fusing readily with non-infected CD4+ lymphocytes, forming giant multi-nucleate syncytia (Crowe). There is also evidence of macrophage involvement in HIV infection of the CNS (Koenig).

It can be appreciated from the foregoing how the selective viral inhibition effects produced by scRIPs, in accordance with the present invention, can be applied to treating HIV infection in humans. The ability of scRIPs to selectively inhibit HIV replication, as evidenced by substantially complete inhibition of viral antigen expression and reverse transcriptase activity, would reduce the level of infection by reducing the production of new virus capable of infecting new cells. Further, inhibition of viral replication may help to eliminate the virus "reservoir" which may be provided by the monocyte/macrophages and other cells. In this regard, it is noted that at least one scRIP—TCS—appears to be able to cross the blood/brain barrier (Hwang) and thus should be effective against the spread of HIV infection to the CNS.

Secondly, evidence discussed above suggests that the fusion of CD4+ T cells with infected T cells or monocyte/macrophages requires the presence of HIV antigens on the surface of the infected cells. One striking effect of the anti-HIV proteins is the ability to inhibit and substantially eliminate expression of viral antigens in infected cells. Substantial reduction in the expression of viral proteins would be expected to be associated with a marked reduction in the cytopathogenic consequences of infection.

Another therapeutic advantage of HIV treatment with scRIPs, in accordance with the invention, is the selective inhibition of HIV-infected T cells. Since infected T cells have the potential to fuse with noninfected T cells, to cause accelerated depletion of the total T cell population, selective destruction of the infected cells should limit the extent of "secondary" T cell destruction.

The anti-HIV proteins can also be expected to inhibit or prevent other events related to the loss of immunological competence in HIV infected individuals, through general suppression of virus levels and inhibition of viral protein synthesis in infected cells.

The dose level of an scRIP which will be therapeutically effective will depend on a variety of factors which can be readily monitored in a treated human subject. Selective inhibition of HIV replication and cellular proliferation in T cells has been observed at scRIP doses as low as 0.01 ug/ml, particularly for the fungal-derived scRIPs tested. For some scRIPs, or for more acute stages of infection, dose levels up to 1 ug/ml or more may be required. However, even with long term exposure to the scRIP, concentrations in the 1-2 ug/ml range are not severely inhibitory in noninfected cells (Section IV). Concentrations of scRIP in the bloodstream of between 0.01 and 1 ug/ml, assuming an approximately 3.50 liter plasma volume, can be achieved by administering a total scRIP dose of between about 0.03 to 3 mg of the scRIP. In the case of TCS, this dose compares with the 5-12.5 mg dose of TCS which is used for inducing abortion in humans, and this dosage level is not generally associated with serious side effects in humans (Kuo-Fen; Hwang).

In the treatment method of the invention, an scRIP is administered to an HIV-infected no line break subject, at a dose which is effective to produce a measurable decrease in at least one of the following indications of HIV infection:

(a) HIV antigen levels associated with HIV-infected T cells or mononuclear phagocytic lineage cells;

(b) HIV antigen levels in the bloodstream;

(c) the reverse transcriptase activity associated with HIV-infected T cells or mononuclear phagocytic lineage cells;

(d) the ratio of viability of HIV-infected to uninfected T cells; and (e) the ratio of a selected HIV antigen to a selected cellular antigen in HIV-infected mononuclear phagocytic lineage cells.

Preferably, the indication of HIV inhibition which is monitored is plasma antigen levels, e.g., serum or plasma p24 levels which can be readily followed using an ELISA procedure. Preferably, the decrease in indication(s) is measurable within 1–5 days after the compound administration. The method may further include alternatively measuring the decrease in at least one of the indications, and repeating the scRIP administering, until the measured indication of HIV infection shows no further decrease.

When a series of doses are administered, e.g., over a several-week period, the patient should be monitored for allergic response to the anti-HIV protein. If a serious response does develop to the first-administered scRIP, e.g., TCS, a second scRIP, e.g., MMC, can be administered to minimize immunological reaction and neutralization of the protein. Preliminary animal data developed by one of the inventors suggest that the two proteins are substantially immunologically non-cross reactive. However, since many patients who would be receiving the treatment are seriously immune compromised, immune response to the proteins may be a relatively minor side effect.

The protein may be administered parenterally in one of a variety of delivery forms, including solution form, liposome-encapsulated form, and attached to a carrier, such as an anti-T cell, anti-macrophage, or anti-HIV antibody, for targeting the protein to HIV-infectable or infected cells. Methods for preparing and storing peptide drug formulations of various types, and for administering the formulation by intravenous, intramuscular, subcutaneous, mucosal membrane, and inhalation routes are known in the pharmaceutical industry.

The following examples illustrate various methods and uses of the present invention, and typical anti-HIV effects observed in the screening method of the invention. The examples are intended to illustrate, but in no way limit, the scope of the invention.

Materials

A. Reagents

[3]H-thymidine and $^3$H-leucine were obtained from New England Nuclear; and fluoroscein isothiocyanate (FITC) conjugated goat-anti-human IgG reagent, from Zymed (Burlingame, Calif.); Anti-p24 monoclonal antibody was provided by Dr. J. Carlson, UC Medical Center, Davis, Calif.

B. HIV isolates

The DV strain of HIV was used for all experiments involving in vitro infection of monocyte/macrophages from noninfected donors. This is a lowpassage isolate obtained from the peripheral blood of a heterosexual man with Kaposi's sarcoma (Crowe). Several liters of the high titre stock of the virus were grown in the VB T lymphoma cell line (Lifson, et al, 1986 a-c), and aliquots were stored at $-70°$ C. until used. Stock cultures of HIV-DV contained about $5 \times 10^5$ infectious units /ml, where an infectious unit is defined as the amount of infectious virus required to produce characteristic cytopathic effects (CPE) by day 5 of culture, when inoculated onto $5 \times 10^5$ VB indicator cells. Stock cultures contained about $89 \times 10^3$ cpm of reverse transcriptase activity, as measured by published methods (Hoffman). Other experiments, as specified, utilized monocyte/macrophages obtained from HIV-infected donors. In these experiments, the HIV isolate employed was the autologous isolate in the particular patient. For T cell studies, the HXB-2 isolate of HIV was used.

C. T Cells

H9 T lymphocyte cells were derived from the H9 cell line (Popovic) VB cells, a T lymphoblastoid cell line were obtained from Dr. S. Smith (Stanford University). Fluorescence activated cell sorting using a fluorescent-labeled anti-CD4 antibody, was used to obtain a strongly CD4-expressing subline of VB. The cells were maintained in RPMI-1640 supplemented with 10% (v/v) heat inactivated fetal calf serum.

D. Monocyte/Macrophaqes

Human macrophage cultures were established from peripheral blood mononuclear cells obtained from leukophoresis preparations of human blood, and buffy coats from normal blood donors, according to established methods (Crowe). Briefly, peripheral blood mononuclear cells were isolated by density centrifugation over Ficollhypaque, and allowed to attach to glass petri dishes in RPMI 1640 medium supplemented with 20% fetal calf serum at 37° C. for 1 hour. After washing (to remove contaminating, non-adherent lymphocytes), the monocytes were recovered from the petri dishes by placing on ice for 10 minutes in 5 uM EDTA-PBS, 5%FCS medium and scraping with a rubber policeman. The recovered monocyte preparation was then centrifuged, resuspended in RPMI 1640 medium with 10% pooled male HIV-negative human serum (complete medium) and placed into Teflon ® culture vessels at $2 \times 10^6$ cells per ml. Cell viability decreased over the first five days in culture to a stable density of approximately $5 \times 10^5$ cells per ml. Long term cultures were maintained at this density for up to four months. Medium was routinely changed every 7 days.

E. Ribosome Inactivating Proteins

1. Trichosanthin

Figure 1A:
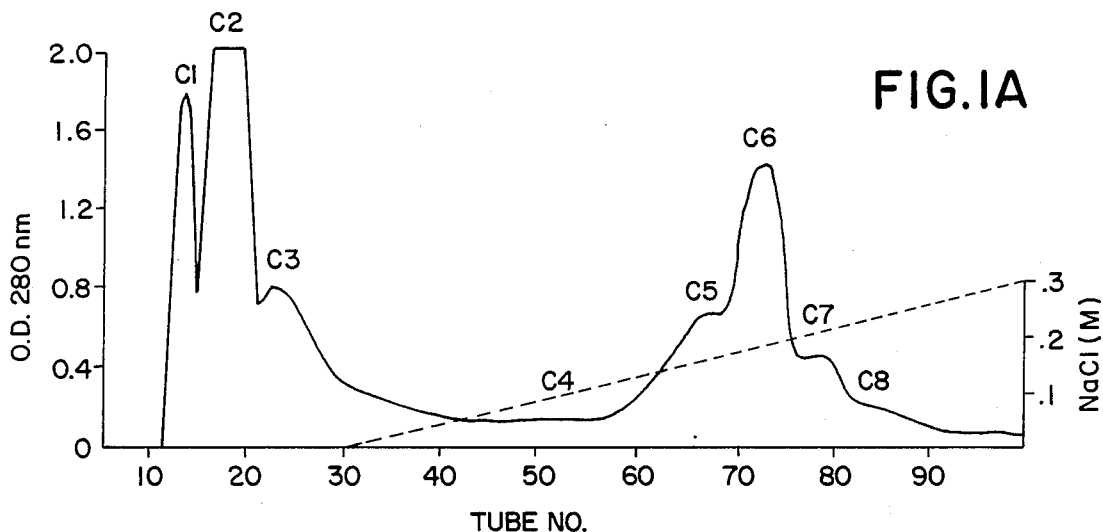
Figure 1B:
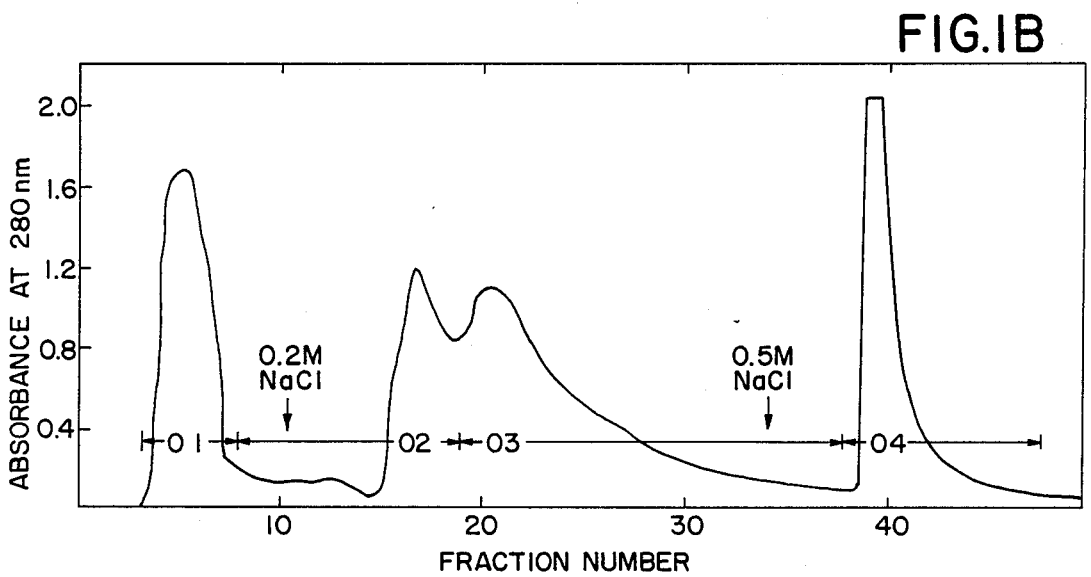
Figure 1C:
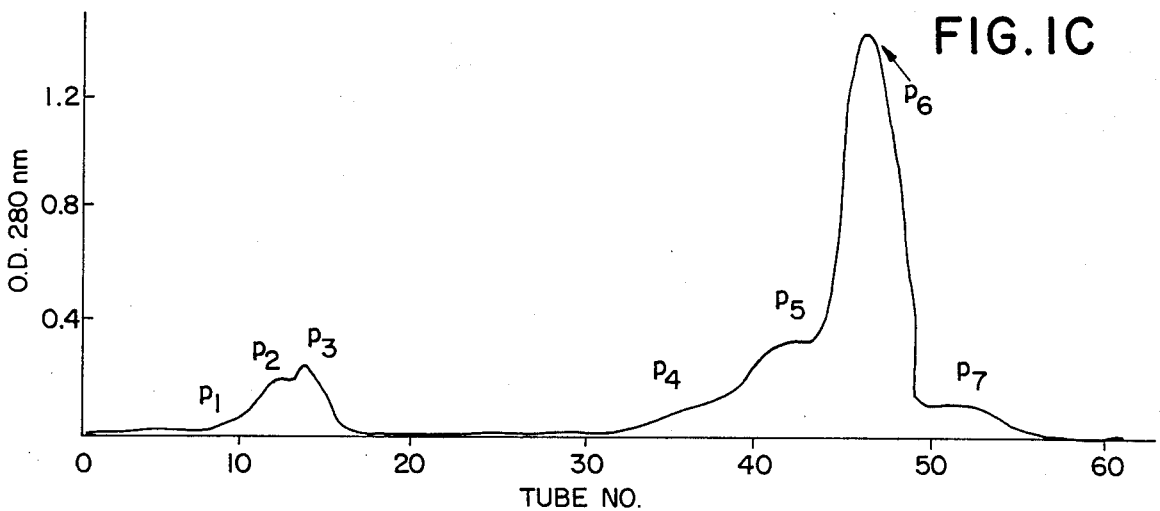

Trichosanthin (TCS) is a plant protein which is obtained from the *Trichosanthes kirilowii* root tuber. The protein, which is also known as alpha-trichosanthin (Law) and Radix trichosanthis (Kuo-Fen), is a basic, single-chain protein consisting of between about 224 (Gu) to 234 (Xuejun) amino acid residues, and having a molecular weight of about 24,000 daltons. One preferred purification method for obtaining TCS in purified form is outlined in Example 1 below. This method involves three chromatograpic separations which are shown in FIG. 1. The protein sequence of TCS has been completed (Gu; Wang), and a molecular model has been derived from cytofluorographic X-ray analysis (Kezhan).

2. Momorcharin

Morocharin (MMC) is a basic glycoprotein obtained from the seeds of the bitter melon plant *Momordica charantia*. The protein appears to have two related forms which have been designated alpha and beta momorcharin. Alpha-momorcharin has a reported molecular weight of between about 31,000 to 32,000 daltons and a neutral sugar content of about 1.6%. Beta-momorcharin has a reported molecular weight of about 29,000 daltons and a neutral sugar content of about 1.3% (Chan). Both forms of momorcharin are effective in inhibiting HIV antigen expression in HIV-infected T lymphocytes and monocyte/macrophages, according to the invention. Momorcharin is defined herein to include both alpha and beta momorcharin, as well as active portions of these proteins which are effective in inhibiting HIV antigen expression in HIV-infected blood cells. The plant glycoprotein can be isolated to homogeneity by fractionating an acetone extract from the seeds of M. charantia on CM Sepharose CL-6B, and Sephadex G100, according to published methods (Yeung, 1985), and as detailed in Example 2 below. FIG. 2 shows the three chromatographic separations involved in the MMC. The proteins are homogeneous on fractionation by HPLC on a TSK250 gel permeation column, SDS gel electrophoresis and immunoelectrophoresis.

Momorcharin appears to be related and perhaps even identical to one or more M. charantia inhibitors ("MCI") having molecular weights in the 30,000 to 32,000 dalton range, and possessing ribosome-inhibitory activity in cell-free systems. Such inhibitors which have been described in the literature are a *Momordica charantica* inhibitor, having molecular weights of 31,000 daltons (Falasca) or 30,000 daltons (Spreafico); "agglutinin", having a molecular weight of about 32,000 daltons (Lin 1970, 1978); and possibly one or more of the four subunits (molecular weights 30,500, 29,000, 28,500 and 27,000 daltons) in a hemaglutinating lectin obtained from the seeds of *M. charantia* (Barbieri, 1980).

It is noted that the MCI which has been most extensively studied as a ribosome inactivating protein was originally characterized as a 23,000 dalton protein, although a subsequent molecular weight determination yielded a molecular weight of about 31,000 daltons (Falasca).

3. Pokeweed Antiviral Protein-I (PAP-I)

PAP-I is a plant, single-chain protein of approximately 27,000 daltons molecular weight. The protein was supplied by Dr. James D. Irvin and was prepared from the pokeweed plant *Phytolacca americana*, according to published methods (Irvin, 1975). Briefly, *P americana* leaves otained from young plants were homogenized in distilled water, filtered, and the filtrate brought to 40% ammonium sulfate and centrifuged to remove precipitated material. The resulting supernatant was chromatographed by DEAE ion-exchange chromatography. A protein peak which contained all of the PAP protein inhibitory activity was further fractionated by phosphocellulose ion-exchange chromatography. The peak which eluted at 0.12M KCl and which contained the bulk of the protein inhibitory activity was used.

4. Pokeweed Antiviral Protein-II (PAP-II)

PAP-II is another single-chain ribosome-inhibitory protein obtained from *P. americana*. The protein is a single polypeptide chain of approximately 29,000 daltons molecular weight. The protein was supplied by Dr. James D. Irvin and was prepared by published methods (Irvin, 1980), involving a modification of the purification method for obtaining PAP-I. Briefly, the elution fractions from the final phosphocellulose column used in the PAP-I purification gave two major peaks of protein inhibitory activity. The first peak corresponds to PAP-I. The second peak was taken as PAP-II. Like PAPI, the PAP-II protein strongly inhibits eukaryotic protein synthesis in a cell-free system, and also inhibits tobacco mosaic virus transmission. The two proteins are distinct, however, in their molecular weights, tryptic peptide maps, and immunological properties.

5. Pokeweed Antiviral Protein-S (PAP-S)

PAP-S is a third distinguishable single-chain ribosome-inhibitory protein obtained from *P. americana*. The protein is a single polypeptide chain of molecular weight about 30,000 daltons. The protein was supplied by Dr. James D. Irvin and was prepared by published methods (Barbieri). PAP-I, PAP-II, and/or PAP-S, are also referred to more generally herein as "pokeweed antiviral protein".

6. Alpha-Sarcin

Alpha-sarcin is a fungal, single-chain polypeptide of approximately 17,000 daltons molecular weight (Sacro). The protein was supplied by Dr. R. Amils, Universidad Autonoma de Madrid, Madrid, Spain and can be obtained from *Aspergillus giganteus*, according to published methods (Olson, 1963a, 1965b). Briefly, a fermentation of *A. giganteus* was filtered through a plate and frame press and the washed extract was adsorbed onto a column of carboxylic acid resin equilibrated to pH 7.0. Elution at 1.5M KCl gave two peaks with alpha-sarcin activity, and these were concentrated, combined, and treated with activated charcoal to remove some contaminating proteins. The crude material was further fractionated on a carboxylic acid ion-exchange resin, using a 0.4M to 0.9M phosphate buffer gradient. Alpha-sarcin eluted as a substantially pure protein.

7. Restrictocin

Restrictocin, like alpha-sarcin, is a fungal, single-chain polypeptide chain of approximately 17,000 daltons molecular weight. The protein was supplied by Dr. R. Amils and can be obtained from *Aspergillis restrictus* by published methods (Olson, 1963).

8. Mitogillin

Mitogillin is a related fungal protein which also has a molecular weight of about 17,000 daltons. The protein was supplied by Dr. R. Amils, and can be obtained from *Aspergillis restrictus* according to published methods (Olson, 1966).

EXAMPLE 1

Preparation of trichosanthin

All steps of the procedure described below were carried out at 4° C. Fresh root tubers of *T. kirilowii* were peeled, sliced into small pieces, and homogenized in a Waring blender in normal saline at pH 7 (0.7 l/kg). The homogenate was filtered through cheesecloth to remove debris. The extract was adjusted to pH 8 with 1N NaOH, stirred for 2 h, and then left to stand overnight. The suspension was centrifuged at 5,000 rpm for 15 min, and the resulting supernatant was adjusted to pH 8 with 1N NaOH. After standing for 1 h, cold acetone (0.8 ug/ml solution) was added. A heavy precipitate resulted and the mixture was stirred for 30 min. The precipitate (AP1) was collected by centrifugation at 5,000 rpm for 15 min. To the supernatant cold acetone (1.2 ug/ml supernatant) was added and after standing for 2 h, the sedimented material (AP2) was recovered by centrifugation. The two fractions AP1 and AP2 were suspended in a minimal volume of phosphate-buffered saline (PBS) and after extensive dialysis against the same buffer, the supernatant and the precipitate of each fraction were separated by centrifugation. The precipitate was then reextracted with PBS, centrifuged and the supernatant combined with the previous supernatant to form the subfraction S, while the precipitate after the reextraction formed the subfraction P. Thus, fraction AP1 gave two subfractions AP1S and AP1P. The yields of the various fractions are: 3.2 g AP1S; 3.8 g AP2S from 1 kg of sliced fresh tuber.

Fraction AP2S (1 g) was dissolved in about 10 ml of 0.05M phosphate buffer (pH 6.4) and applied to a column of CM-Sepharose CL-6B (Pharmacia). The column had previously been equilibrated with 0.05M phosphate buffer, and initial elution was with the same buffer. After the third peak C3 (FIG. 1A) had been eluted, a linear gradient of 0–0.3M NaCl in the same buffer was applied, as seen in FIG. 1A. The protein peak designated C6 was collected, dialyzed against distilled water, and lyophilized to yield highly purified trichosanthin. The average yield and percentage recovery of trichosanthin from AP2S are about 180 mg (18%).

Highly purified trichosanthin was also obtained from fraction AP1S by an additional chromatographic step with DEAE-Sepharose Cl-6B column. AP1S (1 g) was dissolved in 14 ml distilled water. After dialysis against 0.02M $NH_4HCO_3$ containing 0.1M NaCl (pH 8.0), it was applied to a column of DEAE-Sepharose CL-6B (1.5×32 cm) previously equilibrated with the same buffer. Column chromatography was carried out at room temperature at a flow rate of 70 ml/h and the eluate was collected in 10 ml fractions. The column was washed with 100 ml of the starting buffer (0.02M $NH_4HCO_3$) containing 0.1M NaCl and then stepwise elution was performed with 0.2M NaCl and 0.5M NaCl in the same bicarbonate buffer. Elution was monitored by absorbance at 280 nm. The eluate was pooled into four fractions D1–D4 (identified in FIG. 1B), dialyzed and lyophilized. The average yield and percentage recovery of the trichosanthin-enriched fraction D1 from AP1S is about 185 mg (18.5%).

The trichosanthin-enriched fraction D1 was further purified on a CM-Sepharose CL-6B column by a similar procedures as described above for AP2S. The protein peak designated P6 (FIG. 1A) was collected and stored at −70° C., or dialyzed against distilled water, and lyophilized to yield highly purified trichosanthin. The average yield and percentage recovery of trichosanthin from D1 (1 g) is about 445 mg (44.5%).

The combined (from AP2S and D1) yield and percentage recovery of trichosanthin from 1 kg of sliced fresh tuber of *T. kirilowii* are about 900 mg (0.09%)

EXAMPLE 2

Preparation of alpha and beta momorcharin

Figure 2A:
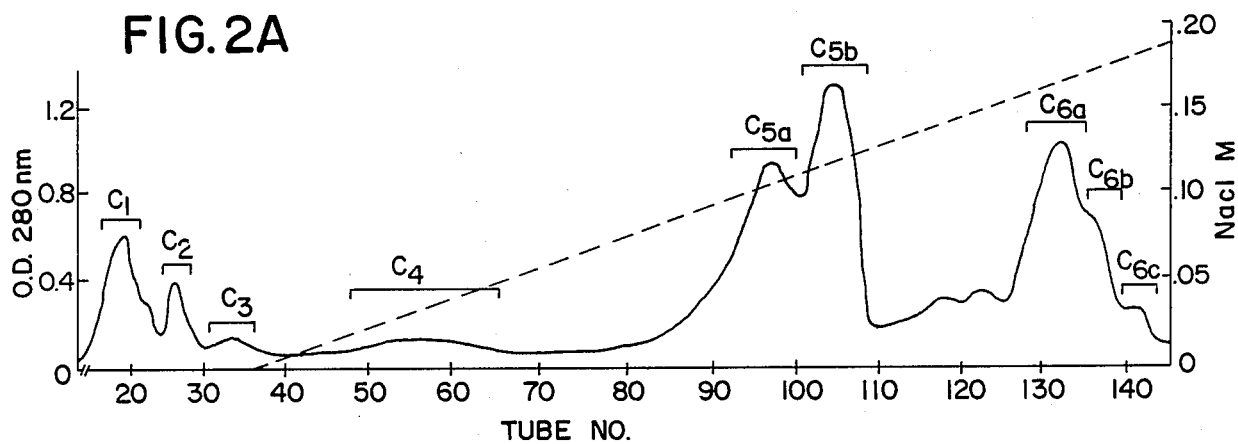
Figure 2B:
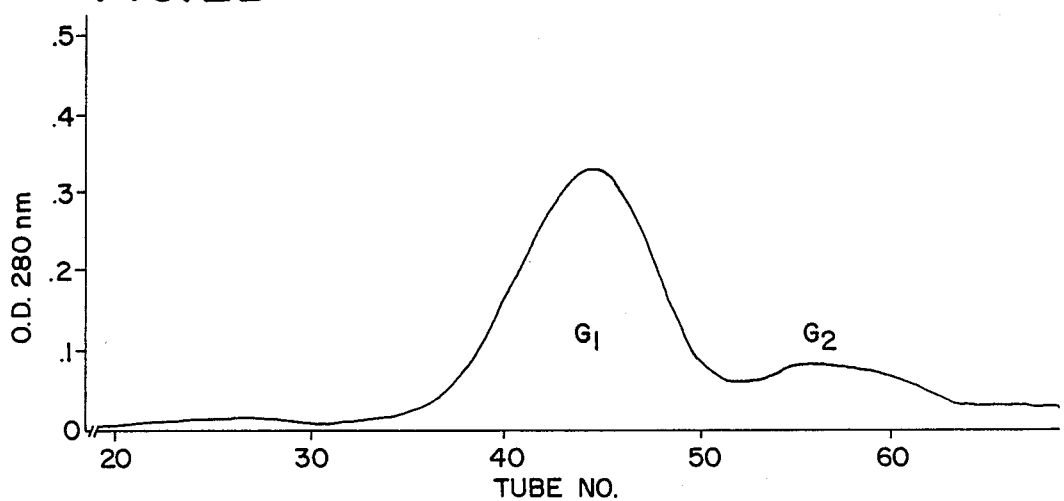
Figure 2C:
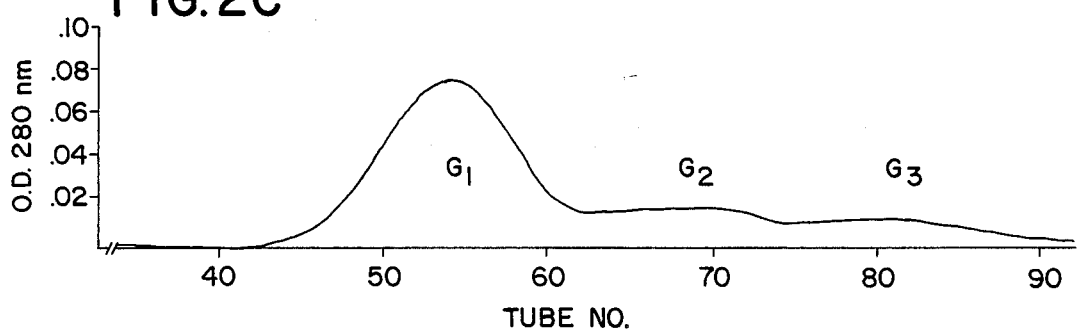

Decorticated dried ripe seeds (100 g) of *Momordica charantia* were homogenized in 0.9% saline (about 4 ml per 1 g) with a Waring Blender and filtered through cheesecloth. The pH of the filtrate was adjusted to 4.0 with 2N HCl before centrifugation at 12,000 rpm for 20 min. The supernatant (crude extract) was then subjected to acetone fractionation at 4° C. To the crude extract, 0.8 v/v of cold acetone (−20° C.) was slowly added with constant stirring and the mixture was kept at 4° C. for 1 h before centrifuged at 5,000 rpm for 15 min to remove the precipitate (API). Cold acetone (−20° C.) was then added to the supernatant to achieve a final concentration of 2.0 v/v. After standing at 4° C. for 1 h, the mixture was centrifuged at 5,000 rpm for 15 min to recover the precipitate (APII) which was resuspended in and dialyzed against 0.05M phosphate buffer (pH 6.4) and applied to a column of CM-Sepharose CL-6B (Pharmacia) equilibrated with the same buffer. Initial elution was with the same buffer. After the third peak had been eluted, a linear gradient of 0–0.2M NaCl in the same buffer was applied, as seen in FIG. 2A, which shows the elution profile from the column. The protein peaks designated $C_{5b}$ and $C_{6a}$ a were collected, and stored at −70° C., or dialyzed against distilled water, and lyophilized. The average yields and percentage recoveries from APII are: $C_{5b}$ (136 mg, 17%) and $C_{6a}$ (76 mg, 9.5%).

The protein fractions $C_{5b}$ (50 mg) and $C_{6a}$ (50 mg) were separately dissolved in 2.5 ml phosphate-buffered saline (pH 7.2) and the undissolved precipitates removed by centrifugation before being applied onto a Sephadex G-100 (fine) (Pharmacia) column equilibrated and eluted with the same buffer. The major protein peaks designated $C_5$-$G_1$ (peak $G_1$ in FIG. 2B) and $C_6$-$G_1$ (peak $G_1$ in FIG. 2C) were collected, and stored at −70° C., or dialyzed against distilled water and lyophilized to yield alpha-momorcharin ($C_5$-$G_1$) and beta-momorcharin ($C_6$-$G_1$), respectively. The average yields and percentage recoveries from $C_{5b}$ and $C_{6a}$ are: alpha-momorcharin (35 mg, 72%) and beta-momorcharin (32 mg, 64%).

Yields and percentage recoveries of alpha-momorcharin and beta-monocharin from 1 kg of decorticated dried seeds of *Momordica charantia* are about 800 mg (0.08%) and 400 mg (0.04%), respectively.

EXAMPLE 3

Effect of TCS and MMC on HIV Antigen Expression in HIV-Infected T Cells

Figure 3A:
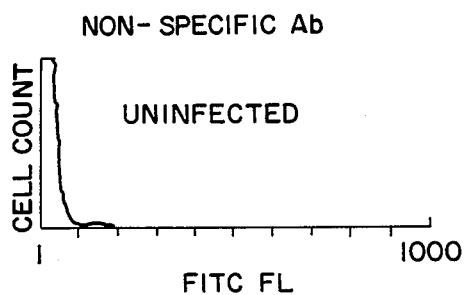
Figure 3B:
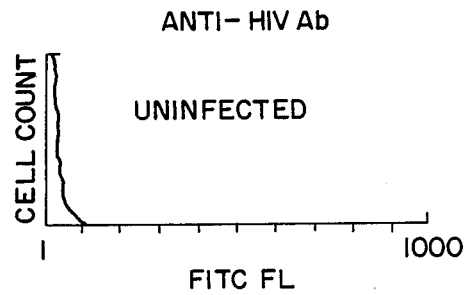
Figure 3C:
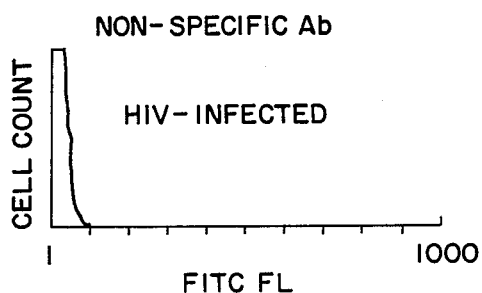
Figure 3D:
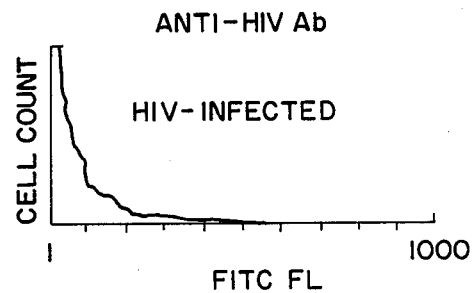
Figure 3E:
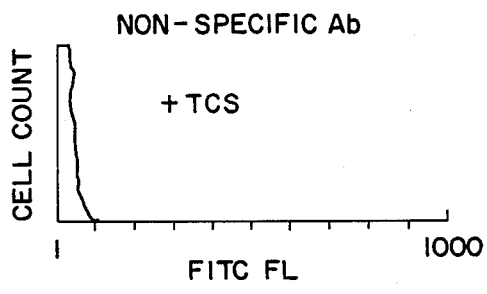
Figure 3F:
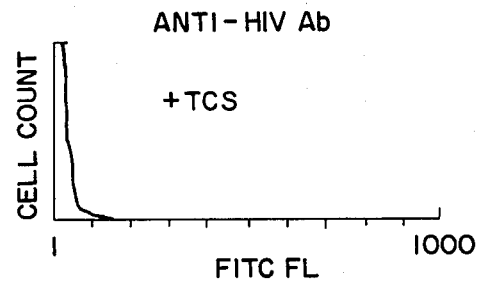
Figure 3G:
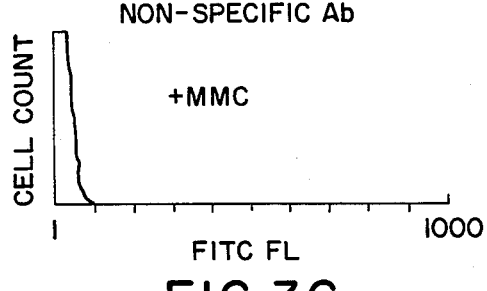
Figure 3H:
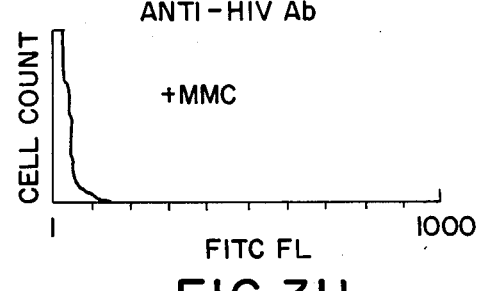

To evaluate the effect of TCS and alpha MMC on viral antigen expression (including expression of the pathogenetically significant envelope antigens gp 120 and gp 41), HIV-infected H9 cells were seeded at $0.5 \times 10^6$/ml and cultured in RPMI-1640 supplemented with 10% heat inactivated fetal calf serum, in the presence of TCS or alpha-MMC at concentrations ranging from 0.3 to 10 ug/ml. Culture medium was replaced every 3–5 days with fresh medium containing additional TCS or alpha-MMC to maintain the specified concentration. At various time points, cells were assayed for expression of HIV antigens by indirect immunofluorescence analysis. Briefly, for each assay, $1 \times 10^6$ cells were washed with phosphate buffered saline containing 1% HI-FCS (staining buffer). Cells were then incubated with a 1:50 dilution of previously characterized HIV antibody positive or negative serum in staining buffer at 4° C. for 45 minutes. After washing, bound specific antibody was detected with a fluorescein conjugated goat anti-human IgG reagent. Quantitative flow cytometric analysis was performed on an Ortho Cytofluorograf 50 H. FIGS. 3A to 3H show the results of flow cytometric analysis performed at day 16 of culture. FIGS. 3A and 3B demonstrate the lack of reactivity of the HIV antibody negative (3A) and antibody positive (3B) patient serum with uninfected H9 cells. FIGS. 3C and 3D show specific reactivity of the antibody positive serum with HIV infected cells (3D) while HIV antibody negative serum does not react (3C). The antibody negative serum does not react with HIV infected cells treated with 10 ug/ml of TCS (3E) or a-MMC (3G). The antibody positive serum shows only background levels of reactivity (approximately 2% or fewer cells showing above threshold fluorescence) with the TCS treated (3F) and a-MMC treated (3H) HIV infected cells, indicating the virtual absence of viral antigen expression by the treated cells. This dramatic phenomenon is noted most strikingly upon comparing FIG. 3D with FIGS. 3F and 3H.

EXAMPLE 4

Effect of scRIP on HIV p24 Antigen Expression in HIV-Infected T cells

VB cells were treated with the indicated concentrations of scRIP concomitant with inoculation with infectious, cell-free HIV virus. Cells were seeded at $0.5 \times 10^6$/ml and cultured in RPMI-1640 supplemented with 10% heat inactivated fetal calf serum, in the continued presence of a selected concentration of TCS, alpha-MMC, PAP-I, PAP-II, PAP-S, mitogillin, restrictocin or alpha-sarcin. The scRIP concentrations are shown along the ordinate in FIGS. 4–6.

Cells were cultured for 3–5 days, and observed for development of characteristic HIV-induced cytopathology (Lifson, 1986a). Cell-free supernatants were harvested and tested using a commercially available ELISA format HIV antigen assay to assess viral replication, by measuring levels of HIV p24 core protein.

Figure 4:
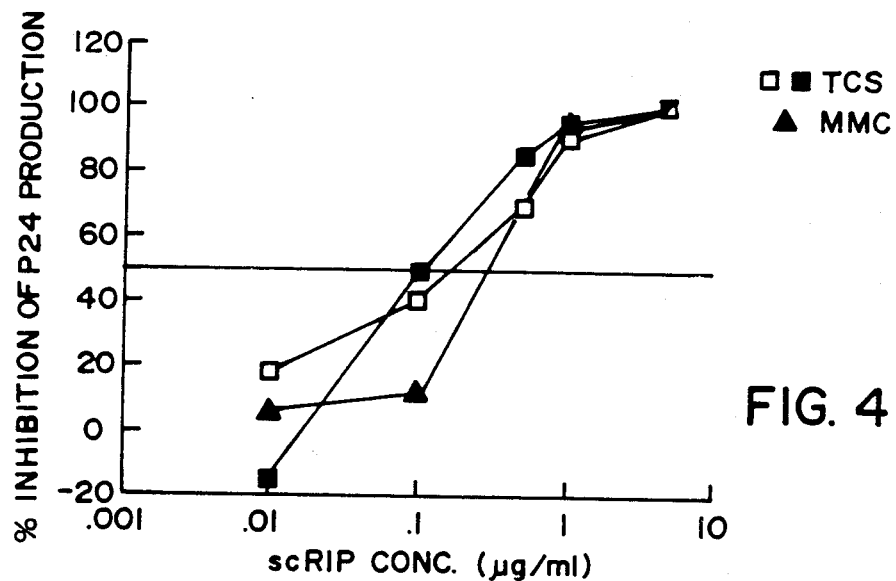

FIG. 4 shows the level of p24 produced by infected T cells, expressed relative to those produced by untreated infected cells, as a function of increasing concentrations of TCS (open and closed squares) and alpha-MMC (triangles). Essentially complete inhibition of viral antigen expression was achieved at an scRIP concentration of between 0.5 and 1 ug/ml for both MMC and TCS.

Figure 5:
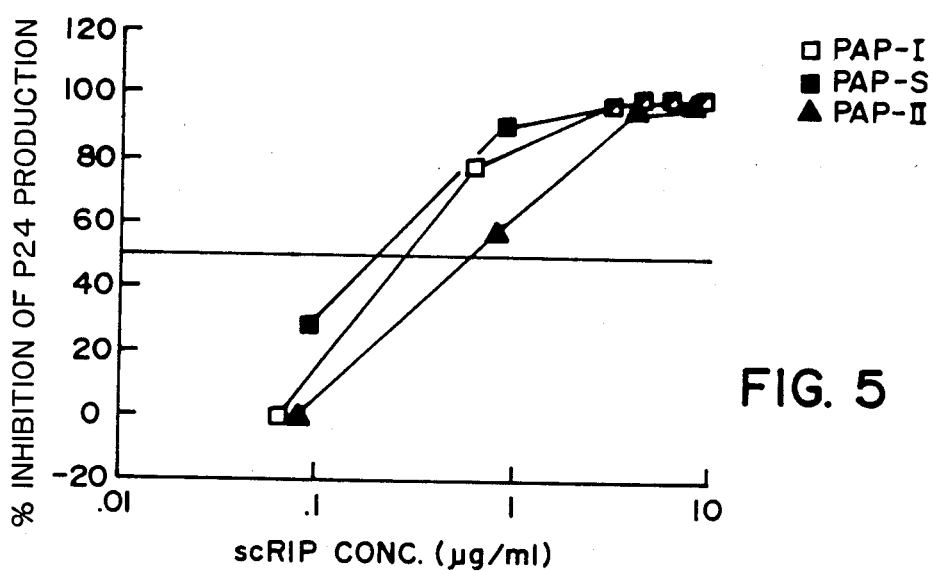

FIG. 5 shows the level of p24 produced by infected T cells, expressed as in FIG. 4 as a function of increasing concentrations of PAP-I (open squares), PAP-II (triangles) and PAP-S (closed squares). The results are similar to those seen in FIG. 4, although somewhat higher concentrations of PAP scRIP compounds were required to effect the same level of antigen inhibition.

Figure 6:
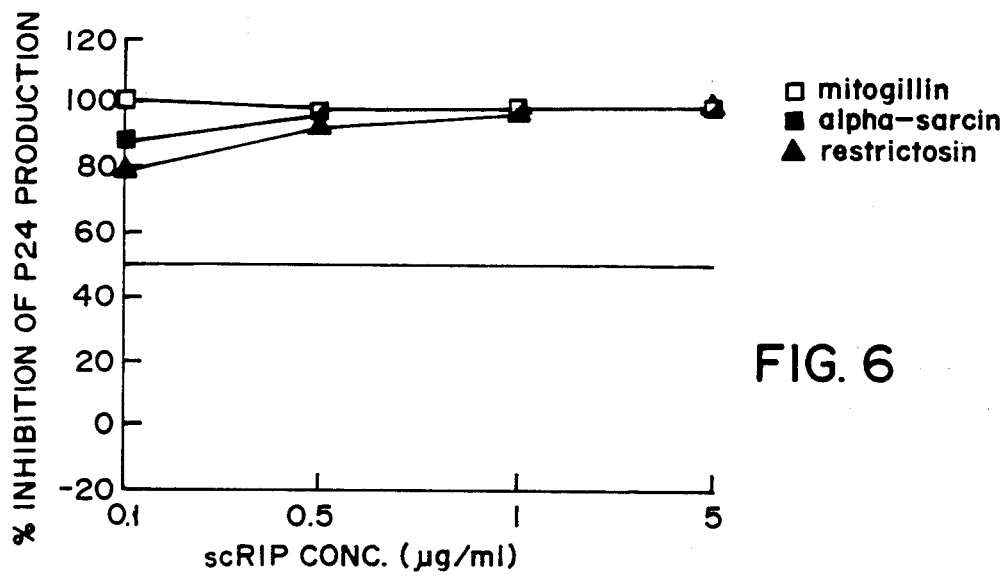

FIG. 6 shows the level of p24 produced by infected T cells, expressed as in FIGS. 4 and 5 as a function of increasing concentrations of mitogillin (open squares), restrictocin (triangles), and alpha-sarcin (closed squares). For all three scRIP compounds, substantially complete p24 inhibition was achieved at 0.5 ug/ml concentration.

EXAMPLE 5

Effect of TCS and MMC Treatment on HIV Replication in Infected T cells

HIV replication was also assessed by measuring particle associated reverse transcriptase activity in cell-free supernatants of cultues. Infected and noninfected cells were seeded and exposed to several selected concentrations of TCS or alpha-MMC as above. At 2 and 5 days after exposure to the drug, the cell suspensions were collected and pelleted by centrifugation at $500\times g$ for 10 minutes. The supernatant was then centrifuged at 45,000 g for one hour and reverse transcriptase (RT) activity was measured as described (Hoffman).

The results obtained for supernatants harvested on day 5 are plotted, as a function of concentration of the scRIP added, in FIG. 7. Uninfected cells (solid circles) showed no detectable RT activity. Both TCS (solid diamonds) and MMC (open squares) treatment resulted in significant, concentration dependent decreases in the amount of viral replication in the cultures, as assessed by measuring particle associated RT activity in cell free culture supernatants. At high concentrations of TCS virtually no RT activity was detected, particularly when one allows for the small amount of virus produced during the first several hours of treatment before the anti-HIV agents have had a chance to exert their effects.

EXAMPLE 6

Infection of Monocyte/Macrophages by HIV

A. Percent cells infected

Monocyte/macrophages were isolated and cultured as above. To infect the macrophage cells with HIV, the macrophages were pelleted by centrifugation after 5–15 days in culture, then resuspended in PBS with 2 ug/ml of polybrene, followed by incubation at 37° C. for 30 minutes. After washing and centrifugation, the pelleted cells were resuspended in HIV-DV, at a concentration of $5\times10^5$ macrophages and $5\times10^5$ infectious units per ml. Cells were left in contact with the virus overnight at 37° C., then unbound virus was washed away, and the cells were resuspended at $5\times10^5$ cells per ml in complete medium.

The frequency of HIV infected macrophages was determined by cytofluorographic, single-cell, indirect immunofluorescence, as described (Crowe), and as outlined in Example 4 above. FIG. 8 shows plots of cell counts as a function of fluorescence level for HIV-infected cells labeled with control (MOPC-21) antibody (A) or anti-p24 antibody (B). The data indicate that about 60% of the cells in the infected macrophage are reactive with anti-p24 antibody ten days after in vitro infection. A level of about 40–60% infected cells was routinely achieved with cells from other donors.

B. Long-term cell viability

To determine whether HIV-infected macrophages continue to survive long-term in culture, the cells were examined for p24 antigen expression over a several week period. The time course of p24 expression in infected macrophage cells from 2 different donors (open circles and triangles) is plotted in FIG. 9. As seen, p24 antigen expression increases rapidly over the first two weeks following infection (time zero), then continues at a relatively high level for at least about 4 weeks. Viability of infected cells from the two donors (closed circles and triangles in FIG. 7) was also examined, using trypan blue exclusion. The infected cells show almost no loss of viability over a four-week period in culture. No cytopathic effects were observed in the infected cells over the test period.

EXAMPLE 7

Effect of TCS and MMC on HIV p24 Antigen Expression in HIV-Infected Monocyte/Macrophages

A. Inhibition of p24 HIV Antigen Expression

Cultured macrophages prepared as above were carried in culture for 7 days, then exposed to TCS or MMC, at a final concentration of 5 ug/ml. Four days after addition of the drug, the cells were examined for p24 expression, as above, by indirect immunofluorescence with anti-p24 antibody. FIG. 10 shows the cytofluorographic profile of (A) control (uninfected) cells, (B), infected cells which were not exposed to drug, (C) infected, TCS-treated cells, and (D) infected, MMC-infected cells. As seen, four days of treatment with either drug reduces p24 expression in infected cells to near background levels.

FIG. 11 shows a similar inhibition of p24 antigen expression by TCS in HIV-infected monocyte/macrophages. Here the cells were exposed to 0.3 ug/ml TCS either at day zero in culture (closed circles) or after four days of culture (closed squares). As seen, the presence of TCS at time zero prevented expression of HIV antigen p24 in the cells, and TCS was also effective in reducing existing p24 levels to near zero four days after cell exposure to the inhibitor.

B. Time Course of TCS and MMC Action

Cultured macrophages infected with HIV were treated with 5 ug/ml of TCS or MMC as in A above. At 1 and 4 days after addition of the drug, the cells were examined for expression of p24 antigen, by t above indirect immunofluorescence method. The data plotted in FIG. 12 show that about 2/3 of inhibition of p24 antigen expression occurs within 24 hours for both TCS (open triangles) and MMC (open circles). RT activity, measured as above, was also markedly decreased after 24 hours in cells treated with either drug. By day four, both p24 expression and RT activity were reduced to background levels, whereas untreated, HIV-infected cells showed no decrease in p24 expression (closed circles in FIG. 11) and no decrease in RT activity. Cell viability, as measured by the trypan blue exclusion test, was reduced to between about 60-70% during the four-day treatment with either drug.

C. Dose Response to TCS and MMC

TCS or MMC was added to cultures of the infected cells at dose levels of either 0.5 or 5 ug/ml. The cells were examined for p24 expression four days after addition of the selected drug, as above. The results are plotted in FIG. 13. As seen, both drug concentrations gave nearly complete inhibition of p24 expression four days after addition of either TCS (triangles) or MMC (open circles).

To determine the response of the infected cells to lower concentrations of scRIP, the infected cells were exposed to MMC concentrations ranging from 0.005 to 5 ug/ml, for 3 hours. MMC was then washed out, and the cells were examined for inhibition of p24 expression 4 days after initial exposure to the scRIP. The results are shown in FIG. 14. Inhibition of HIV antigen expression was greater than 80% even at 0.005 ug/ml.

D. Selective Inhibition of HIV Antigen Expression

To test whether inhibition of HIV p24 antigen expression mediated by TCS in vitro would be specific for HIV proteins, a standard HIV inhibition assay with chronically infected macrophages was performed. In this experiment, $1.5 \times 10^5$ macrophage per well were treated with various concentrations of TCS ranging from 5 nanograms per ml to 5 micrograms per ml for three hours, at which time free TCS was washed out of the culture. Treated and control cells were evaluated 4 days later. As shown in earlier experiments, pulse treatment of HIV infected macrophages with TCS substantially reduces the level of p24 protein expression even at a TCS concentration of 50 nanograms per ml. In the present study, the effect of TCS exposure on expression of cellular proteins and to a specific cellular antigen, HLA-DR, was also examined.

HLA-DR is normally detected on the surface of HIV infected macrophages at approximately 450 fluorescein units per cell (using directly fluoresceinated anti-DR monoclonal antibody as a staining reagent). No substantial decrease in the amount of DR was detected on the surface of HIV infected macrophages with TCS treatment. Even with TCS at a concentration of 5 ug/ml, there was no demonstrable decrease in the amount of cell surface DR antigens detected post-treatment, whereas HIV p24 decreased in a parallel assay by more than 70%, with measurable anti-HIV p24 effects of a 40% inhibition detected at 50 mg/ml. Similarly, parallel cultures treated with TCS were pulsed for 3 hrs with 3H-leucine (20 uCi/ml) 4 days after exposure to the TCS and radioactivity incorporated into protein was determined by TCA precipitation. No inhibition of 3H-leucine uptake was seen at any dose of TCS.

EXAMPLE 8

Inhibition of Cellular Proliferation of HIV-Infected T Cells by TCS and MMC

A. Cellular incorporation of 3H-thymidine

Noninfected H9 T cells or cells chronically infected with HIV, as above, were seeded in 96-well plates ($2.5 \times 10^4$ cells per well in a total final volume of 200 ul of RPMI-1640 supplemented with 10% (v/v) heat inactivated fetal calf serum. TCS or MMC were added to yield final concentrations ranging from 0.01 to 1 ug/ml. After a three-day incubation at 37° C. in a humidified incubator supplied with 5-7% $CO_2$, cultures were pulsed for 12 hours with 1 uCi/well of 3H-thymidine. After the 12 hour pulse period, cultures were harvested onto glass fiber filters by washing the plate wells with distilled water, and the filters were counted by liquid scintillation counting. Data are expressed as percent inhibition of radiolabel incorporation, relative to positive controls containing no test compound.

The data obtained for TCS exposure are plotted in FIG. 15 for noninfected (H9) and HIV-infected (H9.HIV) cells. The TCS concentration corresponding to the intersection between each curve and the 50% inhibition line indicates the TCS concentration effective to cause 50% inhibition of cellular proliferation, as evidenced by a 50% inhibition of thymidine uptake into DNA. The ratio of TCS concentrations needed to produce 50% inhibition in noninfected and HIV infected cells is defined as the selectivity index, and for TCS, is between about 50-60 in the continuous presence of the inhibitor. That is, approximately 50-60 times more TCS is required to produce a comparable level of inhibition in noninfected cells as in HIV-infected T cells. A similar selectivity index was observed for MMC. These selectivity indices were obtained in the continuous presence of scRIP. Greater selectivity is observed with pulsed exposure, as described below. Comparable selectivity indices for 3H-leucine incorporation into noninfected and infected T cells, for both TCS and MMC treatment, were also observed.

B. Time of TCS and MMC Exposure

Noninfected H9 T cells or cells chronically infected with HIV were treated with TCS or MMC at 2 ug/ml. At various time points (5, 15, 30, 60, 120 minutes) of exposure, aliquots of treated cells were washed to remove free TCS and MMC, and the cells were seeded in 96-well microtiter plates, as above, at $2.5 \times 10^4$ cells/well. Cells were cultured for three days, then pulsed for 12 hours with 1 uCi/well of 3H-thymidine. After the 12 hour pulse period, cultures were harvested. $^3$H-thymidine incorporation into cellular DNA was measured by scintillation counting as above. Data are expressed as percent inhibition of radiolabel incorporation, relative to positive controls containing no test compound.

The data obtained for TCS and MMC exposure are plotted in FIGS. 16A and 16B, respectively. As seen, exposure to TCS or MMC for 1 hour or more produces greater than 50% inhibition of cellular proliferation in infected cells, whereas in noninfected cells, no significant inhibition was observed even after two hours of exposure to the added scRIP. Thus with limited (as opposed to continuous) exposure to the inhibitor, the selective inhibition of cellular proliferation of HIV-infected cells (Example 8A) is further enhanced.

C. Effects on cell growth and viability

Cell growth and viability were assessed 2 and 5 days after addition of anti-HIV agents. Cell counts were performed using a hemocytometer and viability was determined by trypan blue exclusion. As shown in FIGS. 17A and 17B, TCS and MMC treatment resulted in a concentration dependent inhibition of cellular proliferation (absolute count of viable cells/ml) at both days 2 and 5, with a preferential inhibition of the proliferation of HIV infected cells. FIG. 17C demonstrates that the percentage of viable cells in the treated cultures was decreased in a concentration dependent manner, with preferential effects on the HIV infected cells. Thus, the growth and viability of the cells appear to be impaired by both cytocidal (decreased percentage of viable cells) and cytostatic (decreased absolute cell counts and decreased percentage of viable cells) mechanisms.

EXAMPLE 9

Effect of scRIP on Cellular Proliferation in HIV-Infected and noninfected T cells The effect of several selected scRIP compounds on cellular proliferation in noninfected and HIV-infected T cells was examined, substantially according to the radiolabel uptake methods described in Example 8A. Specifically, cells were seeded in 96-well plates, then exposed to a selected concentration of the scRIP being tested for a three-day incubation period. The cells were then exposed to $^3$H-thymidine or $^3$H-leucine, at radiolabel concentrations of 1 uCi/well, for 12 hours, before harvesting the cells and counting incorporated radiolabel. As above, data are expressed as percent inhibition of radiolabel incorporation, relative to positive controls containing no test compound.

Figure 19:
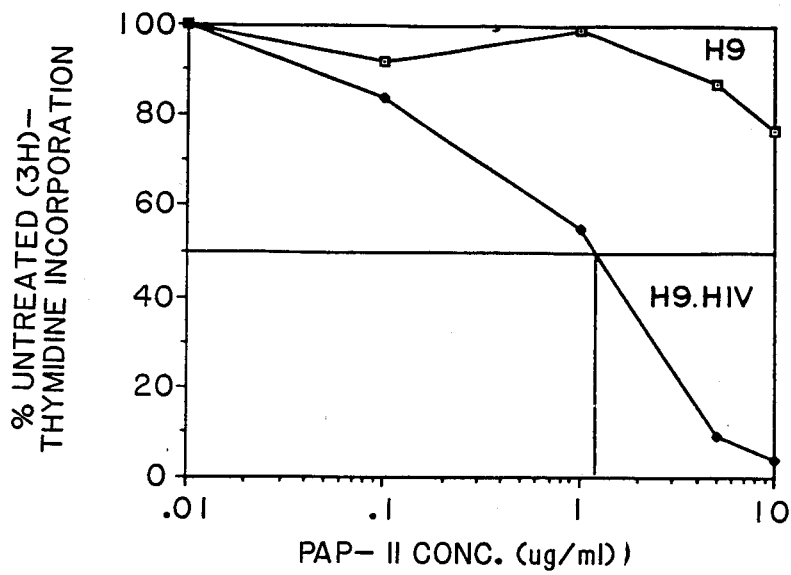
FIG. 19 shows the extent of inhibition of cellular proliferation, as measured by percent $^3$H-thymidine incorporation into cellular DNA in HIV-infected T cells (H9.HIV) and uninfected cells (H9), as a function of PAP-II concentration.

FIG. 18A shows the selective inhibition of cellular proliferation, effected by PAP-I treatment as evidenced by thymidine incorporation in noninfected and HIV-infected T cells. The selectivity index, as defined above, is between 50-60. FIG. 18B shows a similar selective inhibition by PAP-I of leucine incorporation into infected and noninfected T cells. FIG. 19 shows a similar result for thymidine incorporation in infected and noninfected T cells exposed to PAP-II.

Figure 20:
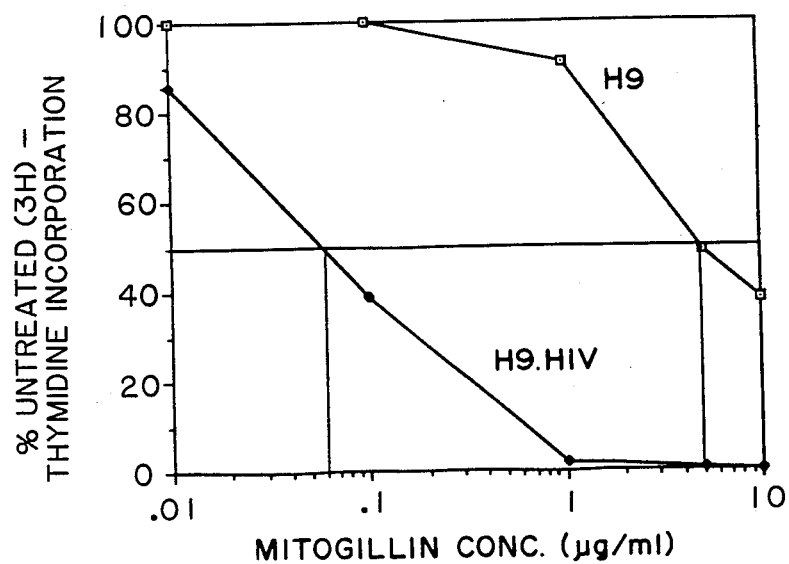
FIG. 20 shows the extent of inhibition of cellular proliferation, as measured by percent 3H-thymidine incorporation into cellular DNA in HIV-infected T cells (H9.HIV) and uninfected cells (H9), as a function of mitogillin concentration.
Figure 21:
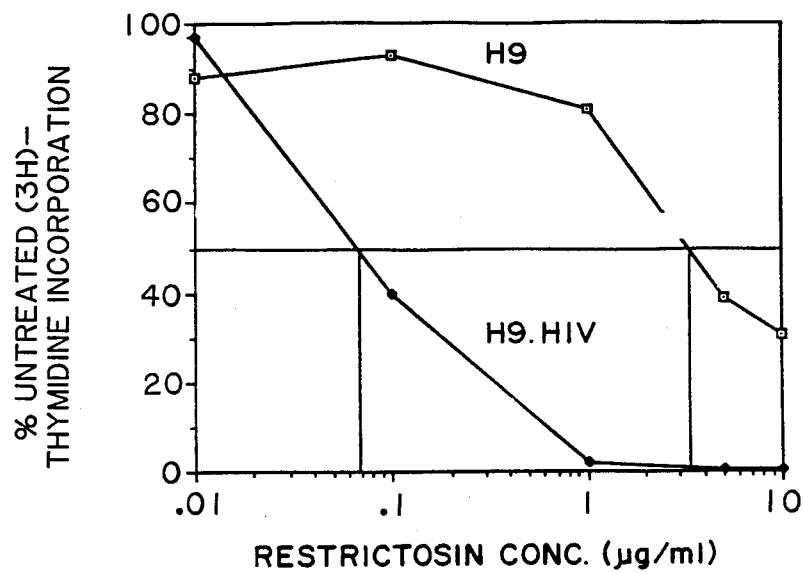
FIG. 21 shows the extent of inhibition of cellular proliferation, as measured by percent $^3$H-thymidine incorporation into cellular DNA in HIV-infected T cells (H9.HIV) and uninfected cells (H9), as a function of restrictocin concentration.

FIGS. 20–22 are similar plots of inhibition of thymidine incorporation into infected and non-infected cells exposed to mitogellin (FIG. 20), restrictocin (FIG. 21) and alpha-sarcin (FIG. 22). In each case, 50% percent inhibition of thymidine uptake into HIV-infected cells occurred at scRIP concentrations of about 0.05 ug/ml, and the selectivity index was about 100.

EXAMPLE 10

Inhibition of Cellular Proliferation of HTLV-I -Infected T Cells by TCS and MMC

A. Cellular incorporation of 3H-thymidine

HTLV-I infected producer cell line $C_{91}$/PC was obtained from Dr. Gregory Reyes, Genelabs Incororated (Redwood City, Cailf.). H9 cells, a continuous cell line not infected with any known retrovirus served as a negative control cell line.

Noninfected H9 T cells or C91/PC cells chronically infected with HTLV-I were seeded in 96-well plates as in Example 7A. TCS, MMC, or mitogillin were added to yield final concentrations ranging from 0.05 to 5 ug/ml. After a three-day incubation at 37° C. in a humidifier incubator supplied with 5–7% $CO_2$, cultures were pulsed for 12 hours with 1 uCi/well of $^3$H-thymidine. After the 12 hour pulse period, cultures were harvested onto glass fiber filters, and thymidine incorporated into cellular DNA was measured as above. Data are expressed as percent inhibition of radiolabel incorporation, relative to positive controls containing no test compound.

The data obtained for TCS exposure are plotted in FIG. 23A for noninfected (H9) and HTLV-I-infected (C91/PL) cells. As seen, there is no significant difference in cellular proliferation, as measured by thymidine incorporation, between nfected and non-infected cells, at any concentration of TCS. Non-selective inhibition of cellular proliferation at increasing concentrations of TCS were observed.

Similar results were obtained for MMC (FIG. 23B) and mitogillin (FIG. 23C), showing no selective inhibitory effect on HTLV-I-infected cells, and a nonselective increase on cellular proliferation with increasing concentrations of either scRIP.

Although the invention has been described with respect to specific embodiments, uses and methods, it will be recognized that various changes, and modifications may be made without departing from the invention.

It is claimed:

1. A method of inhibiting HIV infection in human T lymphocyte cells and mononuclear phagocytic lineage cells infected with HIV, comprising
exposing the infected cells to a single-chain ribosome inactivating protein, at a concentration of the inactivating protein which is effective to inhibit viral antigen expression in the HIV-infected cells.

2. The method of claim 1, wherein said exposing is carried out at a concentration of the inactivating protein and for a duration which is effective to inhibit expression of HIV p24 antigen.

3. The method of claim 1, wherein said exposing is carried out at a concentration of the inactivating protein and for a duration which is effective to selectively inhibit expression of HIV antigens in HIV-infected mononuclear phagocytic lineage cells, as evidenced by a decrease in the ratio of a selected HIV antigen to a selected cellular antigen.

4. The method of claim 1, wherein said inactivating protein is selected from the group consisting of plant-derived single-chain ribosome inactivating proteins, and fungal-derived single-chain ribosome inactivating proteins.

5. The method of claim 4, wherein said inactivating protein is selected from the group consisting of pokeweed antiviral protein, alpha-sarcin, mitogillin, and restrictocin.

6. The method of claim 1, wherein the concentration of ribosome inactivating protein to which the infected cells are exposed is between about 0.01 and 5 ug/ml.

7. A method of selectively inhibiting cellular proliferation of HIV-infected T cells, comprising
exposing the infected cells to a single-chain ribosome inactivating protein, at a concentration of the inactivating protein which is effective to selectively reduce the viability of HIV-infected T cells with respect to noninfected T cells.

8. The method of claim 7, wherein said inactivating protein is selected from the group consisting of plant-derived single-chain ribosome inactivating proteins, and fungal-derived single-chain ribosome inactivating proteins.

9. The method of claim 8, wherein said inactivating protein is selected from the group consisting of pokeweed antiviral protein, alpha-sarcin, mitogillin, and restrictocin.

10. The method of claim 7, wherein the concentration of ribosome inactivating protein to which the infected cells are exposed is between about 0.01 and 5 ug/ml.

11. A method of selectively inhibiting HIV antigen expression in HIV-infected mononuclear phagocytic lineage cells comprising
exposing the infected cells to a single-chain ribosome inactivating protein, at a concentration of the inactivating protein and for a duration which is effective to decrease in the ratio of a selected HIV antigen to a selected cellular antigen in the infected cells.

12. The method of claim 11, wnerein the concentration of ribosome inactivating protein to which the infected cells are exposed is between about 0.005 and 1 ug/ml.

13. The method of claim 12, wherein said inactivating protein is selected from the group consisting of plant-derived single-chain ribosome inactivating proteins, and fungal-derived single-chain ribosome inactivating proteins.

14. The method of claim 13, wherein said inactivating protein is selected from the group consisting of pokeweed antiviral protein, alpha-sarcin, mitogillin, and restrictocin.

15. A method of treating a human subject infected with HIV, comprising
administering a single-chain ribosome inactivating protein to the subject, at a dose which is effective to produce a measurable decrease in at least one of the following indications of HIV infection:
(a) HIV antigen levels associated with HIV-infected T cells or mononuclear phagocytic lineage cells;
(b) HIV antigen levels in the bloodstream;
(c) the reverse transcriptase activity associated with HIV-infected T cells or mononuclear phagocytic lineage cells;
(d) the ratio of viability of HIV-infected to uninfected T cells; and
(e) the ratio of a selected HIV antigen to a selected cellular antigen in HIV-infected mononuclear phagocytic lineage cells.

16. The method of claim 15, wherein said decrease in indication(s) is measurable within 1-5 days after said administration.

17. The method of claim 15, which further includes alternatively measuring the decrease in at least one of said indications, and repeating said administering, until the measured indication of HIV infection shows no further decrease.

18. The method of claim 15, wherein the ribosome inactivating protein is administered parenterally, at a dose which is effective to inhibit HIV antigen expression associated with HIV-infected T cells or mononuclear phagocytic lineage cells.

19. The method of claim 15, wherein said inactivating protein is selected from the group consisting of plant-derived single-chain ribosome inactivating proteins, and fungal-derived single-chain ribosome inactivating proteins.

20. The method of claim 19, wherein said inactivating protein is selected from the group consisting of pokeweed antiviral protein, alpha-sarcin, mitogillin, and restrictocin.

* * * * *

UNITED STATES PATENT AND TRADEMARK OFFICE
CERTIFICATE OF CORRECTION

PATENT NO. : 4,869,903

DATED : September 26, 1989

INVENTOR(S) : Jeffrey D. Lifson et al

It is certified that error appears in the above-identified patent and that said Letters Patent is hereby corrected as shown below:

On the title page,
in the Assignee:

Change "Genelabs Incorporated, Redwood City, Calif." to (add to)---Genelabs Incorporated, Redwood City, Calif. and The Regents of the University of California, Berkeley, Calif.---

Signed and Sealed this

Fifth Day of March, 1991

Attest:

HARRY F. MANBECK, JR.

*Attesting Officer*    *Commissioner of Patents and Trademarks*